US012016334B2

(12) United States Patent
Rudrappa et al.

(10) Patent No.: US 12,016,334 B2
(45) Date of Patent: Jun. 25, 2024

(54) COMPOSITION COMPRISING SULPHATED GALACTOSE, AND IMPLEMENTATIONS THEREOF

(71) Applicant: SEA6ENERGY PVT. LTD., Bangalore (IN)

(72) Inventors: Girish Tavarekere Rudrappa, Bangalore (IN); Hemanth Giri Rao Vantharam Venkata, Bangalore (IN); Pooja Malhotra, Bangalore (IN); Sumit Purushottam Bhose, Bangalore (IN); Narendrakumar Sekar, Bangalore (IN); Sam Kuruvilla, Bangalore (IN); Lekshmi Girija, Bangalore (IN); Sachin Khandelwal, Bangalore (IN); Nithin Sanghe, Bangalore (IN); Sawan Kumar, Bangalore (IN); Sri Sailaja Nori, Bangalore (IN); Shrikumar Suryanarayan, Bangalore (IN)

(73) Assignee: SEA6ENERGY PVT. LTD., Bangalore (IN)

( * ) Notice: Subject to any disclaimer, the term of this patent is extended or adjusted under 35 U.S.C. 154(b) by 867 days.

(21) Appl. No.: 16/955,326

(22) PCT Filed: Nov. 8, 2019

(86) PCT No.: PCT/IN2019/050831
§ 371 (c)(1),
(2) Date: Jun. 18, 2020

(87) PCT Pub. No.: WO2020/095329
PCT Pub. Date: May 14, 2020

(65) Prior Publication Data
US 2023/0210115 A1     Jul. 6, 2023

(30) Foreign Application Priority Data
Nov. 9, 2018 (IN) .............................. 201841042303

(51) Int. Cl.
| | |
|---|---|
| *A01N 41/02* | (2006.01) |
| *A01N 43/16* | (2006.01) |
| *A61K 9/00* | (2006.01) |
| *A61K 31/195* | (2006.01) |
| *A61K 31/60* | (2006.01) |
| *A61K 31/7004* | (2006.01) |
| *A61K 31/7016* | (2006.01) |
| *A61K 31/702* | (2006.01) |
| *A61K 33/22* | (2006.01) |
| *A61K 33/30* | (2006.01) |
| *A61K 36/04* | (2006.01) |
| *A61P 31/00* | (2006.01) |

(52) U.S. Cl.
CPC .............. *A01N 41/02* (2013.01); *A01N 43/16* (2013.01); *A61K 9/0056* (2013.01); *A61K 31/195* (2013.01); *A61K 31/60* (2013.01); *A61K 31/7004* (2013.01); *A61K 31/7016* (2013.01); *A61K 31/702* (2013.01); *A61K 33/22* (2013.01); *A61K 33/30* (2013.01); *A61K 36/04* (2013.01); *A61P 31/00* (2018.01)

(58) Field of Classification Search
None
See application file for complete search history.

(56) References Cited

U.S. PATENT DOCUMENTS

| | | | |
|---|---|---|---|
| 5,472,582 A | * 12/1995 | Jackson | ........... G01N 27/44726 204/461 |
| 10,358,391 B2 | 7/2019 | Nori et al. | |
| 2017/0334794 A1 | 11/2017 | Nori et al. | |

FOREIGN PATENT DOCUMENTS

| | | |
|---|---|---|
| EP | 1175907 A1 | 1/2002 |
| WO | WO 2014/027368 A2 | 2/2014 |

OTHER PUBLICATIONS

Li, M., Shang, Q., Li, G., Wang, X., & Yu, G. (2017). Degradation of marine algae-derived carbohydrates by Bacteroidetes isolated from human gut microbiota. Marine Drugs, 15(4), 92. (Year: 2017).*

Prechoux et al.; "Enzyme-Assisted Preparation of Furcellaran-Like κ-/β-Carrageenan"; Marine Biotechnology; vol. 18; 2016; p. 133-143.

Jung et al.; "Potentials of macroalgae as feedstocks for biorefinery"; Bioresource Technology; vol. 135; May 2013; p. 182-190.

(Continued)

*Primary Examiner* — Dale R Miller
(74) *Attorney, Agent, or Firm* — BakerHostetler

(57) ABSTRACT

The present disclosure discloses a composition comprising: (a) at least one sulphated galactose; and (b) at least one saccharide selected from a group consisting of disaccharide, trisaccharide, tetrasaccharide, pentasaccharide, and salts thereof. The present disclosure further discloses a weight percentage of the at least one sulphated galactose to be in a range of 15-90% with respect to the total sugar content. Further, the present disclosure discloses a use of the composition for protecting/treating plants from infection. Also provided is a use of the composition for protecting/treating animals from infection. The present disclosure discloses a use of sulphated galactose for protecting/treating plants from infection. Also provided is a use of sulphated galactose for protecting/treating animals from infection. The present disclosure also discloses a method for preparing the composition as described herein.

32 Claims, 10 Drawing Sheets

Specification includes a Sequence Listing.

(56) References Cited

OTHER PUBLICATIONS

Vera et al.; "Oligo-carrageenans induce a long-term and broad-range protection against pathogens in tobacco plants (var. *Xanthi*)"; Physiological and Molecular Plant Pathology; vol. 79; 2012; p. 31-39.
International Patent Application No. PCT/IN2019/050831; Int'l Written Opinion and Search Report; dated Jan. 23, 2020;.
Savary et al; "Crop losses due to diseases and their implications for global food production losses and food security"; Food Security; vol. 4; 2012; p. 519-537.
Patier et al.; "Free or silica-bound oligokappa-carrageenans elicit laminarinase activity in Rubus cells and protoplasts"; Plant Science; vol. 110; Sep. 1995; p. 27-35.
Vera et al.; "Long-term protection against tobacco mosaic virus induced by the marine alga oligo-sulphated-galactan Poly-Ga in tobacco plants"; Molecular Plant Pathology; vol. 12; 2011; p. 437-447.
Chattopadhyay; Use of antibiotics as feed additives: a burning question; Frontiers Microbiology; vol. 5; Jul. 2014; 3 pages.
Zuniga et al.; "Preparation of a low-molecular weight fraction by free radical depolymerization of the sulfated galactan from Schizymenia binderi (Gigartinales, Rhodophyta) and its anticoagulant activity"; Carbohydrate Polymers; vol. 66; Oct. 2006; p. 208-215.
Yu et al.; "Structural studies on κ-carrageenan derived oligosaccharides"; Carbohydrate Research; vol. 337; 2002; p. 433-440.
Pandey et al; "Resistance to early blight of tomato with respect to various parameters of disease epidemics"; Journal of General Plant Pathology; vol. 69; 2003; p. 364-371.
Bau et al.; "Broad-Spectrum Resistance to Different Geographic Strains of Papaya ringspot virus in Coat Protein Gene Transgenic Papaya"; Phytopathology; vol. 93; 2003; p. 112-120.
Peat et al.; "926. Sulphates of monosaccharides and their derivatives. Part I. Preparation"; Journal of the Chemical Society; 1960; p. 4761-4766.
Turvey et al.; "407. Sulphates of monosaccharides and derivatives. Part IV. Galactose 4-sulphate"; Journal of the Chemical Society; 1962; p. 2119-2122.
Zuniga et al.; "Preparation of a low-molecular weight fraction by free radical depolymerization of the sulfated galactan from Schizymenia binderi (Gigartinales, Rhodophyta) and its anticoagulant activity"; Carbohydrate Polymers; vol. 66; 2006; p. 208-215.
Mehdi et al.; "Use of antibiotics in broiler production: Global impacts and alternatives"; Animal Nutrition; vol. 4; 2018; p. 170-178.
Yeh et al.; "Immunomodulation by carrageenans in the white shrimp Litopenaeus vannamei and its resistance against Vibrio alginolyticus"; Aquaculture; vol. 276; 2008; p. 22-28.
Sirirustananun et al.; "Dietary administration of a Gracilaria tenuistipitata extract enhances the immune response and resistance against Vibrio alginolyticus and white spot syndrome virus in the white shrimp Litopenaeus vannamei"; Fish & Shellfish Immunology; vol. 31; 2011; p. 848-855.
Kalitnik et al.; "Low molecular weight derivatives of different carrageenan types and their antiviral activity"; J Appl Phycol; vol. 25; 2013; p. 65-72.

\* cited by examiner

COMPOSITION COMPRISING SULPHATED GALACTOSE, AND IMPLEMENTATIONS THEREOF

CROSS REFERENCE TO RELATED APPLICATIONS

This application is a National Stage of International Application No. PCT/IN2019/050831, filed on Nov. 8, 2019, which claims priority to Indian Patent Application No. 201841042303, filed on Nov. 9, 2018, the disclosures of which are incorporated by reference in their entirety.

FIELD OF INVENTION

The present disclosure broadly relates to the field of compositions and particularly relates to compositions comprising sulphated galactose, methods for their formulation and use as defense and remedy for plants and animals against biotic and abiotic stress.

BACKGROUND OF INVENTION

Living organisms, be it plants or animals are always under constant threat from both biotic and abiotic stresses. A biotic stress is an adverse effect resulting from any damage done to a living organism by another living organism, such as viruses, bacteria, fungi, parasites, insects, weeds, other plants or animals. An abiotic stress includes any negative impact on a living organism in a specific environment by a non-living factor, such as temperature, humidity, salt, sunlight etc. For plants, the direct yield losses of about 20 to 40% of global agricultural productivity is estimated to be caused by various biotic stresses (Savary et al., Food Sec. 2012; 4:519). Animals are also under constant threat from both biotic and abiotic stresses. For example, the prevalence of white spot virus disease in farmed shrimp has caused losses of several billions of dollars globally after its incidence (Lightner, D. V. 2003).

There are increasingly evolving threats in terms of pathogens (e.g. bacteria, viruses and fungi) and changing environmental conditions that affect agricultural livelihoods in terms of cultivation of land and breeding of plants and animals. However, conventional methods of protection and treatment of crops and livestock using either direct control of using synthetic chemicals or developing plant and animal pathogen tolerant/resistant varieties by breeding and transgenic approaches are facing more complex and challenging problems with the evolution of pathogens with increasing abilities to combat them.

Further, although, the use of synthetic chemicals has revolutionized the quantity of food being produced, the increasing amounts that need to be used to counter resistance are resulting in high residual levels of chemicals in the final food product, be it plant-based or animal-based. Overall food-chains and ecological systems are getting affected without proper, sustainable counter-measures.

Alternatively, transgenic crops and animals are yet to be adopted into practice in many developing countries while newly-bred resistant varieties become susceptible within short periods of time due to the aforementioned fast evolving pathogen range.

Thus, an underlying opportunity has arisen, which is to address this dire need for developing novel natural solutions for crop and livestock protection and rehabilitation. Such novel alternate solutions may additionally complement existing approaches to crop and livelihood rejuvenation and protection. Moreover, such natural compositions are advantageous in being environment friendly, consistently effective and easier to replicate success with for wider and mom acceptable use world-wide.

Patier el. al., Plant Science 110-(1995) 27-35 discloses carrageenan oligosaccharides, prepared by enzymatic hydrolysis, in which the oligomers consist of repeating units of D-3,6-anhydro-α+-D-galactopyranosyl (1-3)-O-8-D-galactopyranosyl-4-sulphate, (neo-carrabiose) with a polymerisation degree (DP=n) ranging from DP2 (tetrasaccharide) and higher up to DP7, which are obtained by enzymatic hydrolysis of carrageenan and showed that they elicit the activity of plant defense enzymes in *Rubus Fruticosus*. From reading this disclosure and consulting the. FIGS. 2 & 3 (page 30. Col 2) and FIG. 4. (page 31. Col 1), it would seem that the higher molecular weight hexasaccharide (DP3) is more active than the lower molecular weight tetrasaccharide (DP2).

Vera et. al., Physiological and Molecular Plant Pathology (2011) 12(5) 437-447 discloses that the oligo-sulphated galactan of 8,500 Da (Poly-Ga) induces a dose-dependent, treatment-number-dependent and long-term protection against tobacco mosaic virus (TMV) in tobacco plants, mimicking a vaccination effect. Further, Vera et. al., Physiological and Molecular Plant Pathology 79 (2012) 31-39 describes that oligo-carrageenans kappa 2, lambda and iota of 10,000 Da corresponding to around 20 units of sulphated galactose induce a long-term and broad-range protection against pathogens in tobacco plants (var. Xanthi).

Kalitnik et. al., J Appl Phycol (2013) 25:65-72 discloses the low molecular derivatives of different carrageenan types and their antiviral activity. Kalitnik et. al., describes that the derivatives of carrageenan with molecular weights ranging from 1200 Da to 4300 Da can be obtained by different methods. Further, Kalitnik et. al., teaches that the antiviral activity of higher molecular weight carrageenan oligosaccharides against TMV was higher than that of their low molecular weight derivatives. (Page 70, $1^{st}$ column, $2^{nd}$ full paragraph & page 70 $2^{nd}$ column last paragraph)

In the case of animals, Chen et. al. (Aquaculture 2008), reported that when shrimp were injected with various types of carrageenan polymers, an increased resistance towards *Vibrio harveyi*(bacterial) infection was observed as compared to the untreated shrimp. Another publication, Chen et. al. (Fish & Shellfish Immunol, 2014) reported that the inclusion of hot water extract of *Gracilaria tenuistipitata* (sulfated polysaccharide) in the diet fed to white shrimp. *Litopenaeus vannamei* improved resistance towards *Vibrio alginolyticus* bacteria as well as towards white spot syndrome virus, when said challenges were tested. Work done by Cheng et. al. (Fish Shellfish Immunol 2007), showed that iota-carrageenan when injected into fish intraperitoneally followed by a challenge test with *Vibrio alginolyticus* (bacteria) showed higher survival as compared to untreated fish. In addition, while anti-biotics are effective against bacterial infections, anti-biotics have been used as growth promoters when given at very low dosages. The rampant use of antibiotic growth promoters due to the intensive cultivation of livestock, birds and other aquatic animals is resulting in emergence of new antibiotic resistant bacterial strains (M K Chattopadhayay et. al., Front Microbiol. 2014; 5: 334, Y Mehdi et. al., Anim Nutrition 2018). This is another issue that needs to be addressed with alternative products which can improve animal health in a natural way and are environment and consumer friendly.

In view of the prior art mentioned in previous paragraphs, it is clear that there is a dire need to find natural products and compositions, which are environment friendly, effective and at the same time can be dispensed in either a liquid or a solid form to be useful for plant as well as animal protection and therapy against biotic and abiotic stresses. Such compositions will give desired sustainable yet ecologically conscious protection for crops and livestock in agricultural practices for long-term use.

SUMMARY OF THE INVENTION

In an aspect of the present disclosure, there is provided a composition comprising at least one sulphated galactose.

In a second aspect of the present disclosure, there is provided a composition comprising: (a) at least one sulphated galactose; and (b) at least one saccharide selected from a group consisting of disaccharide, trisaccharide, tetrasaccharide, pentasaccharide, and salts thereof.

In a third aspect of the present disclosure, there is provided a composition comprising: (a) at least one sulphated galactose; and (b) at least one saccharide selected from a group consisting of disaccharide, trisaccharide, tetrasaccharide, pentasaccharide, and salts thereof, wherein the at least one sulphated galactose to the at least one saccharide component has a weight ratio in a range of 1:5 to 50:1.

In a fourth aspect of the present disclosure, there is provided a composition comprising: (a) at least one sulphated galactose; and (b) at least one derivative of a saccharide like IMF wherein the at least one sulphated galactose to the at least one saccharide derivative component has a weight ratio in a range of 9:1 to 2:1.

In a fifth aspect of the present disclosure, there is provided a process for preparing the composition comprising: (a) contacting a substance having a mixture of polysaccharides with water to obtain a slurry; and (b) depolymerizing the slurry by hydrolysis to obtain the composition.

In a sixth aspect of the present disclosure, there is provided a use of the composition for the treatment and/or protection of plants.

In a seventh aspect of the present disclosure, there is provided a use of the composition for the treatment and/or protection of animals.

In an eighth aspect of the present disclosure, there is provided a method for treating a plant, said method comprising: (a) obtaining the composition; and (b) contacting the composition with a plant or parts of a plant.

In a ninth aspect of the present disclosure, there is provided a method for treating an animal, said method comprising: (a) obtaining the composition; and (b) administering the composition with an animal or parts of an animal.

In a tenth aspect of the present disclosure, there is provided a method for curing a plant, said method comprising: (a) obtaining the composition; and (b) contacting the composition with a plant or parts of a plant.

In an eleventh aspect of the present disclosure, there is provided a method for curing an animal, said method comprising: (a) obtaining the composition; and (b) contacting the composition with an animal or parts of an animal.

In a twelfth aspect of the present disclosure, there is provided a use of sulphated galactose for protecting plants from infections.

In a thirteenth aspect of the present disclosure, there is provided a use of sulphated galactose for activating plant defense pathway.

In a fourteenth aspect of the present disclosure, there is provided a use of sulphated galactose for protecting animals from infections or abiotic stress.

In a fifteenth aspect of the present disclosure, there is provided a use of sulphated galactose for treating infected plants.

In a sixteenth aspect of the present disclosure, there is provided a use of sulphated galactose for treating infected animals.

In a seventeenth aspect of the present disclosure, there is provided a use of sulphated galactose for stimulating animal immunity and stress tolerance.

These and other features, aspects, and advantages of the present subject matter will be better understood with reference to the following description and appended claims. This summary is provided to introduce a selection of concepts in a simplified form. This summary is not intended to identify key features or essential features of the claimed subject matter, nor is it intended to be used to limit the scope of the claimed subject matter.

BRIEF DESCRIPTION OF ACCOMPANYING DRAWINGS

The following drawings form a part of the present specification and are included to further illustrate aspects of the present disclosure. The disclosure may be better understood by reference to the drawings in combination with the detailed description of the specific embodiments presented herein.

FIG. 1 illustrates *Sclerotinia* infection lesion-based assay on *Arabidopsis thaliana* following foliar spray with a liquid formulation containing Gal-S called formulation Gal-S-L1 at 2, 3, 4 mL/L dilutions, as compared to untreated plants, in accordance with an embodiment of the present disclosure.

FIG. 2 illustrates *Alternaria volani* infection severity scoring assay on tomato plants following foliar spray with a liquid formulation containing Gal-S called formulation Gal-S-L1, as compared to untreated plants, in accordance with an embodiment of the present disclosure.

FIG. 3 illustrates comparative field trials on tomato crop represented as percent reduction in tomato-blight incidence following spraying with a liquid formulation of Gal-S-L1, and a commercially available chemical fungicide containing Azoxystrobin 23% SC, as compared to untreated plants, in accordance with an embodiment of the present disclosure.

FIG. 4 illustrates a qPCR-based assay to quantitate Papaya Ring Spot Virus (PRSV) load reduction in papaya following a foliar spray with a liquid formulations Gal-S-L1 and Gal-S-L12 containing Gal-S at different levels, where Gal-S-L12 was diluted with water at a concentration of 1.5 mL/L, and Gal-S-L1 was diluted with water to a concentration of 4 ml/L and compared to untreated plants, in accordance with an embodiment of the present disclosure.

FIG. 5 illustrates improvement in product efficacy with additives such as metal ions or, salicylic acid or beta aminobutyric acid (BABA) to the formulation containing Gal-S as the major component (89%) of the total sugar component, as compared to untreated plants, in accordance with an embodiment of the present disclosure.

FIG. 6 illustrates the increase in survival of the shrimp *L. vannamei* in outdoor field conditions upon inclusion of Gal-S-L1 in the diet showing that Gal-S containing formulations can alleviate abiotic stresses in animals, in accordance with an embodiment of the present disclosure.

FIG. 7 illustrates that the size of the fungus induced lesion/damage in detached tomato leaves that were treated with Gal-S containing formulations and then infected with *Alternaria Solani* was lower with increase in Gal-S content in the liquid formulations showing the protective effect of Gal-S on plant health in accordance with an embodiment of the present disclosure.

FIG. 11 illustrates that combinations of Gal-S containing formulations with existing anti-fungal compounds with different modes of action (e.g azoxystrobin and dimethomorph) can still provide enhanced protection against pathogen attack for plants, because of its ability to upregulate plant defence pathways in accordance with an embodiment of the present disclosure.

FIG. 12 illustrates how Gal-S containing formulations can upregulate certain gene pathways in plants which are known to play a role in plant defence in accordance with an embodiment of the present disclosure.

Figure 17:
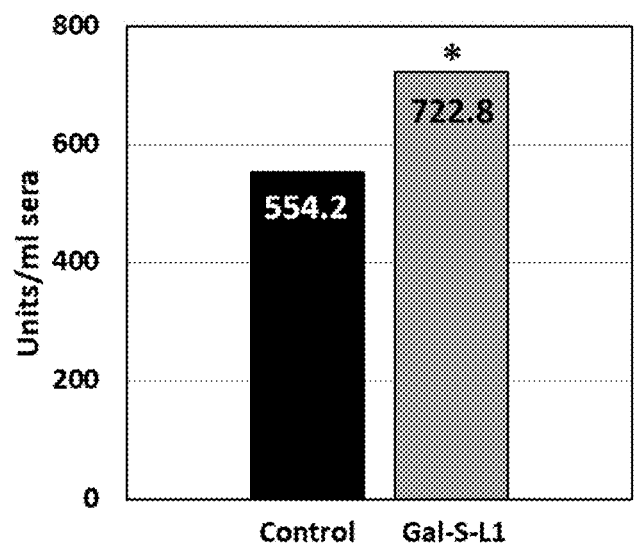

FIG. 17 shows the increase in serum Glutathione reductase enzyme activity upon inclusion of a powder formulation of Gal-S-L1 in the broiler feed as compared to control (* indicates p-value<0.05, ANOVA). The glutathione reductase is a marker of antioxidant activity and an improved antioxidant status can protect an animal from abiotic stresses thus showing the effect of Gal-S containing formulations in accordance with an embodiment of the present disclosure.

Figure 18:
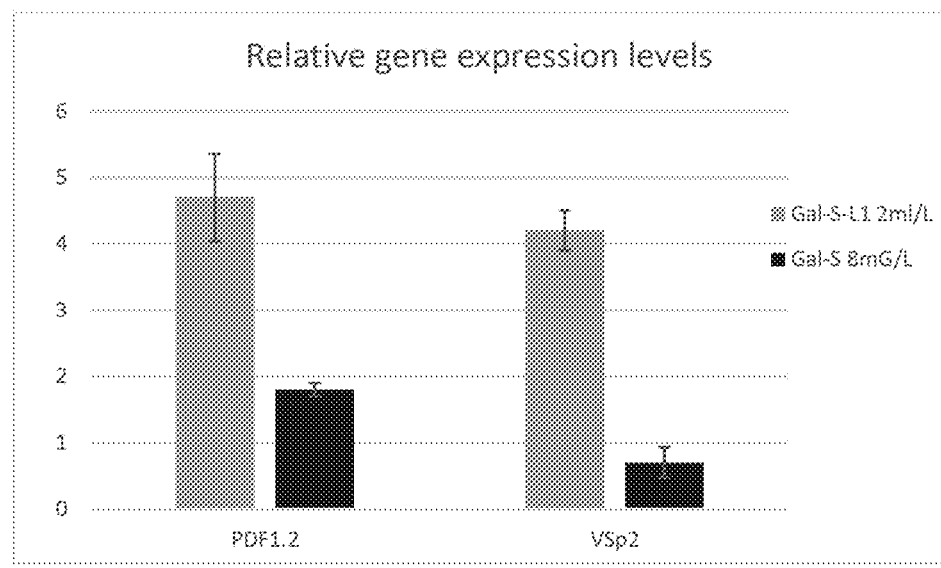

FIG. 18 shows the relative gene expression levels of immune gene markers PDF1.2 and VSP2 in *Arabidopsis* plants upon treatment with Gal-S-L1 formulation and Gal-S at 2 ml/L and 8 mg/L respectively and that a threshold concentration of Gal-S is required in the final application to trigger immune gene expression, in accordance with an embodiment of the present disclosure.

DETAILED DESCRIPTION OF THE INVENTION

Those skilled in the art will be aware that the present disclosure is subject to variations and modifications other than those specifically described. It is to be understood that the present disclosure includes all such variations and modifications. The disclosure also includes all such steps, features, compositions, and compounds referred to or indicated in this specification, individually or collectively, and any and all combinations of any or more of such steps or features.

Sequences used in the present disclosure

SEQ ID NO: 1 depicts forward primer sequence to amplify PRSV NiB gene

AGTCGGCCCGAAGCAATTTT

SEQ ID NO: 2 depicts reverse primer sequence to amplify PRSV NiB gene

CTCATCACACTCAAGATAGTTCCTGAA

SEQ ID NO: 3 depicts forward primer sequence to amplify PDF 1.2 gene.

TCACCCTTATCTTCGCTGCTC

SEQ ID NO: 4 depicts reverse primer sequence to amplify PDF 1.2 gene.

ATGTCCCACTTCGCTTCTCG

SEQ ID NO: 5 depicts forward primer sequence to amplify VSP gene.

TGTGAACAGGCAGATCAACC

SEQ ID NO: 6 depicts reverse primer sequence to amplify VSP gene.

GCGATACCGATCTCGTCAA

SEQ ID NO: 7 depicts forward primer sequence to amplify PR 1 gene.

AATGCTCAAGATAGCCCACAAG

SEQ ID NO: 8 depicts reverse primer sequence to amplify PR 1 gene.

AATAAGTCACCGCTACCCCAG

Definitions

For convenience, before further description of the present disclosure, certain terms employed in the specification, and examples are delineated here. These definitions should be read in the light of the remainder of the disclosure and understood as by a person of skill in the art. The terms used herein have the meanings recognized and known to those of skill in the art, however, for convenience and completeness, particular terms and their meanings are set forth below.

The articles "a", "an" and "the" are used to refer to one or to more than one (i.e., to at least one) of the grammatical object of the article.

The terms "comprise" and "comprising" are used in the inclusive, open sense, meaning that additional elements may be included. It is not intended to be construed as "consists of only".

Throughout this specification, unless the context requires otherwise the word "comprise", and variations such as "comprises" and "comprising", will be understood to imply the inclusion of a stated element or step or group of element or steps but not the exclusion of any other element or step or group of element or steps.

The term "including" is used to mean "including but not limited to". "Including" and "including but not limited to" are used interchangeably.

For the purposes of the present disclosure, the term "at least one saccharide component" is intended to cover any saccharide component known in the general art and any salts or derivates of saccharides thereof. The salts include the general known salts of saccharide in the existing art. Derivatives of saccharides include derivatives like Hydroxymethyl Furfural (HMF) that are formed during the process of hydrolysis. "Total sugar content" is intended to cover sulphated galactose and at least one saccharide component and the derivative of saccharide component of the composition as disclosed in the present disclosure. The "total sugar content" refers in general to all the soluble carbohydrates or sugars in the composition that can be detected using standard tests such as the anthrone sulfuric acid test mentioned in the present disclosure. The term "at least one sulphated galactose" is intended to cover a monosaccharide component and all possible sulphonylation on a galactose moiety, it can be at one place, two places, or three places on the galactose moiety. Additionally, it is intended to cover a mixture of sulphated galactoses which are sulphonylated at different positions. The term "polysaccharides" is intended to cover permutations and combinations of monosaccharide sugars in various degrees of polymerizations (DP). The term "animal feed" is intended to cover all possible feeds that can be given to animals bred under captivity for domestic purposes. The term animal includes but is not limited to: poultry, fish, shrimp, cattle, other aquatic animals, livestock, insects, mammals, reptiles & rodents. The terms "sulphated galactose" and "galactose sulphate" are to be understood interchangeably. The term "plant" is intended to include all types of plants generally known in the art to which the composition of the present disclosure and sulphated galactose can be contacted with. The term "dry form" in relation to the composition of the present disclosure relates to the composition not having more than 10% w/w level of moisture.

Unless defined otherwise, all technical and scientific terms used herein have the same meaning as commonly understood by one of ordinary skill in the art to which this disclosure belongs. Although any methods and materials similar or equivalent to those described herein can be used in the practice or testing of the disclosure, the preferred methods, and materials are now described. All publications mentioned herein are incorporated herein by reference.

Ratios, concentrations, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited.

In view of the prior art mentioned in the Background section, it is clear that none of the prior art ever tested formulations rich in the monosaccharide galactose sulphate for their plant or animal protective and therapeutic effects. Furthermore, from reading all the above literature, a person of skill in the art would conclude that carrageenan oligosaccharides of higher molecular weight would be the most effective in their plant protective effects, thereby lacking any motivation to search for alternatives, especially one based on the lowest in condensation of sugar hierarchy, i.e., monosaccharides. Furthermore, none of the above literature provide any indications that the monosaccharide galactose sulphate alone or a composition comprising said monosaccharide in majority may be able to have plant or animal protective and/or therapeutic effects. In view of the drawbacks associated with conventional methods or transgenic approaches known in the art to protect and cure crops and livestock against biotic and abiotic stresses faced with ever-evolving and changing stress landscape, the present disclosure provides a unique combination of natural ingredients comprising formulations majorly rich in the monosaccharide galactose sulphate, which when combined in predetermined weight concentrations, provides a protective and curative composition which provides an unexpected and surprising results leading to activation of protective systems such as immune response pathways in plants and animals to combat biotic and abiotic stresses. Moreover, a further effective defense against such stresses is produced by addition of trace elements such as certain metal ions. A combinatorial effect is further observed when combining the monosaccharide galactose sulphate-based compositions of the present disclosure with natural plant defense activators such as salicylic acid and/or amino acids such as beta aminobutyric acid. Furthermore it is shown that derivatives of saccharides that are sometimes formed as a result of the hydrolysis conditions, like HMF may provide additional protective effects in their own right Thus, the present disclosure provides an effective, environment friendly solution to address the need in the art for a natural formulation to defend plants and animals against biotic and abiotic stressors. Furthermore, the known formulations in the art, even the ones with oligosaccharides of sulphated galactose, teach an increase in efficacy of protective defense against stressors, for example, anti-viral responses with increasing oligomerization or complexity of said sugars. In contrast, the compositions and formulations of the present disclosure solve the problem by unexpectedly demonstrating the effect of monosaccharide galactose sulphate-based compositions in mounting a strong defense against biotic and abiotic stressors in living organisms, be it plants or animals.

Furthermore, the present disclosure has the advantage of providing a unique, well-characterized, highly reproducible, uniform and scalable composition for use in either a liquid or solid form that is amenable to regulatory approval. The present disclosure also provides a composition with an ease of use with uniformity acceptable to be sold as a commercial product along with an easily identifiable, yet unique and novel active ingredient (monosaccharide galactose sulphate) with an unexpected and surprising effect over biotic and abiotic stresses.

None of the prior art as mentioned in the Background section ever specifically tested formulations rich in the monosaccharide galactose sulphate for their plant protective effects. Also, some of the methods used by the investigators therein, to prepare the carrageenan oligosaccharides may have either not resulted in the formation of galactose sulphate or removed or reduced the concentration of the very low molecular weight compounds, galactose-4-sulphate (MW 282 CAS Number 125113-68-0) or galactose 6-sulphate (MW 282 CAS Number 125455-62-1) or galactose-2,6-disulphate (MW 340). For example, Patier et. al. used an enzymatic method to depolymerize kappa carrageenan which is mainly known to produce oligosaccharides in multiples of a repeating disaccharide unit (κ-carrabiose) and not known to produce monosaccharides. In fact, the smallest unit that Patier et. Al, reported in their publication was a tetra-saccharide (referred therein as DP2), which is composed of two repeating units of κ-carrabiose.

Vera et, at used the method of Zúñiga et. al. (2006) (Preparation of a low molecular weight fraction by free radical depolymerization of the sulphated galactan from *Schyzimenia binderi* (Gigartinales, Rodophyta) and its anticoagulant activity. Carbohydr. Polym. 66, 208-215.). The method of Zúñiga et. al. (2006) involved dialyzing the depolymerized carrageenan extensively through a dialysis membrane of 3,500 MW cutoff (which would remove all the molecular weights below 3,500) and then used the remaining material for further purposes. Vera et. al. (2012) used relatively mild conditions of acid hydrolysis using HCl at 0.1N at 60° C. and for 45 minutes which may not have resulted in extensive formation of monosaccharides. In fact, Vera et. al. specifically analyzed their preparation and determined that the molecular weight was on an average, 10,000 Daltons. Similarly, Kalitnik et. al. (2013) used the method of Yu et. al. (2002—Structural studies on κ-carrageenan derived oligosaccharides. Carbohydr Res 337:433-440), which used acid hydrolysis using 0.1N HC at 60° C. for 4 hours. It is interesting to note that under these conditions, as per FIG. 1 of Yu et. al. (2002), the lowest molecular weight produced was greater than or equal to 2660 Daltons. This is consistent also with Vera el. al. (2012), which used relatively milder conditions of acid hydrolysis using ICI at 0. IN at 60° C. and for 45 minutes. In fact, Vera et. al., specifically analyzed their preparation and determined that the molecular weight was on an average, 10,000 Daltons, which is consistent with the relatively milder conditions used therein.

Thus, it is likely that none of the investigators above may have prepared and tested a carrageenan hydrolysate in which the major components of the total sugars are less than 400 Da by molecular weight.

In the case of animals, Chen et. al. (Aquaculture 2008), reported that when shrimp were injected with various types of carrageenan polymers, an increased resistance towards *Vibrio harveyi* (bacterial) infection was observed as compared to the untreated shrimp. Another publication, Chen et. al. (Fish & Shellfish Immunol, 2014) reported that the inclusion of hot water extract of *Gracilaria tenuistipitata* (sulfated polysaccharide) in the diet fed to white shrimp, *Litopenaeus vannamei* improved resistance towards *Vibrio alginolyticus* bacteria as well as towards white spot syndrome virus, when said challenges were tested. Work done by Cheng et. al. (Fish Shellfish Immunol 2007), showed that iota-carrageenan when injected into fish intraperitoneally followed by a challenge test with *Vibrio alginolyticus* (bacteria) showed higher survival as compared to untreated fish. In all of these cases, depolymerization of the polysaccharides was not carried out. Therefore, the molecular weights of these polysaccharides are much larger than 400 Da.

In all of these studies, there has been no indication that monosaccharide galactose sulphate alone or in combination with other oligosaccharide sulphates could achieve similar effects, and if anything, the idea of higher hierarchy saccharides has been associated with better protection.

The present disclosure is not to be limited in scope by the specific embodiments described herein, which are intended for the purposes of exemplification only. Functionally-equivalent products, compositions, and methods are clearly within the scope of the disclosure, as described herein.

The composition as disclosed in the present disclosure comprises sulphated galactose. In another aspect, the composition comprises sulphated galactose and at least one saccharide component or a derivative of a saccharide. In a separate aspect, the at least one saccharide component is selected from a group consisting of disaccharide, trisaccharide, tetrasaccharide, pentasaccharide, and salts thereof, and combinations thereof. The at least one saccharide component is selected from a group consisting of sulphated salts of disaccharide, trisaccharide, tetrasaccharide, pentasaccharide, and combinations thereof. The composition of the present disclosure discloses a composition rich in sulphated galactose.

In an embodiment of the present disclosure, there is provided a composition comprising at least one sulphated galactose.

In an embodiment of the present disclosure, there is provided composition comprising: (a) at least one sulphated galactose; and (b) at least one saccharide selected from a group consisting of disaccharide, trisaccharide, tetrasaccharide, pentasaccharide, and salts thereof. In another embodiment of the present disclosure, the at least one saccharide component is selected from a group consisting of carrabiose, carratriose, and combinations thereof.

In an embodiment of the present disclosure, there is provided composition comprising: (a) at least one sulphated galactose; and (b) at least one saccharide selected from a group consisting of disaccharide, trisaccharide, tetrasaccharide, pentasaccharide, and salts thereof, wherein the at least one sulphated galactose comprises galactose-4-sulphate. It can be contemplated that all other possible combinations of sulphonylation of galactose are also included in the scope of the present disclosure.

In an embodiment of the present disclosure, there is provided composition comprising: (a) at least one sulphated galactose; and (b) at least one saccharide selected from a group consisting of disaccharide, trisaccharide, tetrasaccharide, pentasaccharide, and salts thereof, or a derivative of a saccharide wherein the at least one sulphated galactose comprises D-galactose-4-O-sulphate.

In an embodiment of the present disclosure, there is provided composition comprising: (a) at least one sulphated galactose; and (b) at least one saccharide selected from a group consisting of disaccharide, trisaccharide, tetrasaccharide, pentasaccharide, and salts thereof, or a derivative of a saccharide wherein the at least one sulphated galactose comprises D-galactose-4-O-sulphate. D-galactose-2-O-sulphate, and D-galactose-6-O-sulphate. In another embodiment of the present disclosure, the at least one sulphated galactose comprises D-galactose-4-O-sulphate, D-galactose-2-O-sulphate, and D-galactose-6-O-sulphate in a weight ratio in a range of 1-100:1-100:1-100.

In an embodiment of the present disclosure, there is provided composition comprising: (a) at least one sulphated galactose; and (b) at least one saccharide selected from a group consisting of disaccharide, trisaccharide, tetrasaccharide, pentasaccharide, and salts thereof, or a derivative of a saccharide wherein the at least one sulphated galactose comprises D-galactose-2-O-sulphate, and D-galactose-2,6-di-sulphate. In another embodiment of the present disclosure, the at least one sulphated galactose comprises D-galactose-2-O-sulphate, and D-galactose-2,6-di-sulphate in a weight ratio in a range of 100:1 to 1:100.

In an embodiment of the present disclosure, there is provided composition comprising: (a) at least one sulphated galactose; and (b) at least one saccharide selected from a group consisting of disaccharide, trisaccharide, tetrasaccharide, pentasaccharide, and salts thereof, and wherein the composition further comprises at least one derivative of a saccharide selected from a group consisting of hydroxy methyl furfural (HMF), levulinic acid, formic acid, and combinations thereof.

In an embodiment of the present disclosure, there is provided a composition as described herein, wherein the at least one sulphated galactose has a weight percentage in a range of 15-90% with respect to the total sugar content. In another embodiment, the at least one sulphated galactose has a weight percentage in a range of 18-88% with respect to the total sugar content. In yet another embodiment, the at least one sulphated galactose has a weight percentage in a range of 20-75% with respect to the total sugar content.

In an embodiment of the present disclosure, there is provided a composition as described herein, wherein the at least one saccharide is selected from a group consisting of kappa-carrabiose, kappa-carratriose, kappa-carratetraose, iota-carrabiose, iota-carratriose, iota-carratetraose, lambda-carrabiose, lambda-carratriose, lambda-carratetraose, and salts thereof or a derivative of a saccharide like HMF In an embodiment of the present disclosure, there is provided a composition as described herein, wherein the composition has a total sugar content in a range of 25-120 g/l. In another embodiment, the composition has a total sugar content in a range of 30-110 g/l. In yet another embodiment, the composition has a total sugar content in a range of 35-100 g/l. In an alternate embodiment, the composition has a total sugar content in a range of 40-100 g/l.

In an embodiment of the present disclosure, there is provided a powder composition as described herein, wherein the composition has a total sugar content in a range of 100-500 g/kg.

In an embodiment of the present disclosure, there is provided composition comprising: (a) at least one sulphated galactose; and (b) at least one saccharide selected from a group consisting of disaccharide, trisaccharide, tetrasaccharide, pentasaccharide, and salts thereof, wherein the composition is in a powder form having a total sugar content in a range of 100-600 g-kg. In another embodiment, the composition is in a powder form having a total sugar content in a range of 150-500 g/kg. In yet another embodiment, the composition is in a powder form having a total sugar content in a range of 150-450 g/kg. In an alternate embodiment, the composition is in a powder form having a total sugar content in a range of 200-450 g/kg.

In an embodiment of the present disclosure, there is provided a composition as described herein, wherein the composition further comprises at least one substance selected from a group consisting of solvent, diluent, emulsifiers, stabilizers, animal feed, and combinations thereof.

In an embodiment of the present disclosure, there is provided a composition as described herein, wherein the composition comprises the at least one sulphated galactose or at least one saccharide having a weight percentage in a range of 5-90% of total solid content of the composition (excluding moisture).

In an embodiment of the present disclosure, there is provided composition comprising: (a) at least one sulphated galactose; and (b) at least one saccharide selected from a group consisting of disaccharide, trisaccharide, tetrasaccharide, pentasaccharide, and salts thereof, wherein the at least one sulphated galactose is having a weight percentage in a range of 5-90% of total solid content of the composition. In another embodiment, the at least one sulphated galactose is having a weight percentage in a range of 10-85% of total solid content of the composition. In yet another embodiment, the at least one sulphated galactose is having a weight percentage in a range of 20-85% of total solid content of the composition. In an alternate embodiment, the at least one sulphated galactose is having a weight percentage in a range of 30-85% of total solid content of the composition.

In an embodiment of the present disclosure, there is provided a composition as described herein, wherein the at least one sulphated galactose to the at least one saccharide component has a weight ratio in a range of 1:5 to 50:1.

In an embodiment of the present disclosure, there is provided composition comprising: (a) at least one sulphated galactose; and (b) at least one saccharide selected from a group consisting of disaccharide, trisaccharide, tetrasaccharide, pentasaccharide, and salts thereof, wherein the at least one sulphated galactose to the at least one saccharide component has a weight ratio in a range of 1:5 to 50:1. In another embodiment, the at least one sulphated galactose to the at least one saccharide component has a weight ratio in a range of 1:1 to 45:1. In yet another embodiment, the at least one sulphated galactose to the at least one saccharide component has a weight ratio in a range of 1:1 to 40:1. In an alternate embodiment, the at least one sulphated galactose to the at least one saccharide component has a weight ratio in a range of 5:1 to 35:1.

In an embodiment of the present disclosure, there is provided composition comprising: (a) at least one sulphated galactose; and (b) at least one saccharide selected from a group consisting of disaccharide, trisaccharide, tetrasaccharide, pentasaccharide, and salts thereof, wherein the at least one sulphated galactose to the at least one saccharide component has a weight ratio in a range of 1:5 to 50:1. In another embodiment, the at least one sulphated galactose to the at least one saccharide component has a weight ratio in a range of 1:5 to 40:1, or 1:2 to 35:1, or 1:1 to 30:1, or 2:1 to 28:1, or 5:1 to 25:1, or 7:1 to 22:1, or 10:1 to 20:1, or 1:1 to 17:1.

In an embodiment of the present disclosure, there is provided a composition comprising: (a) at least one sulphated galactose; and (b) at least one derivative of a saccharide like HMF wherein the at least one sulphated galactose to the at least one saccharide derivative component like HMF has a weight ratio in a range of 9:1 to 2:1.

In an embodiment of the present disclosure, there is provided composition comprising: (a) at least one sulphated galactose; (b) at least one saccharide selected from a group consisting of disaccharide, trisaccharide, tetrasaccharide, pentasaccharide, and salts thereof; and (c) at least one derivative of a saccharide selected from a group consisting of hydroxy methyl furfural (HMF), levulinic acid, formic acid, and combinations thereof, wherein the at least one sulphated galactose to the at least one derivative of a saccharide has a weight ratio in a range of 9:1 to 2:1. In another embodiment, the at least one sulphated galactose to the at least one derivative of a saccharide has a weight ratio in a range of 7:1 to 1:1. In yet another embodiment, the at least one sulphated galactose to the at least one derivative of a saccharide has a weight ratio in a range of 6:1 to 1:1.

In an embodiment of the present disclosure, there is provided a composition as described herein, wherein the composition further comprises at least one additive selected from a trace element, a natural plant defense activator, and combinations thereof.

In an embodiment of the present disclosure, there is provided a composition as described herein, wherein the composition further comprises at least one additive selected from a trace element, a natural plant defense activator, and combinations thereof, and wherein the trace element is selected from a group consisting of boron, zinc, iron, manganese, magnesium, molybdenum, calcium, potassium, selenium, copper combinations thereof and their salts.

In an embodiment of the present disclosure, there is provided a composition as described herein, wherein the composition further comprises at least one additive selected from a trace element, a natural plant defense activator, and combinations thereof, and wherein the natural plant defense activator is selected from a group consisting of salicylic acid, beta amino butyric acid, their salts and combinations thereof.

In an embodiment of the present disclosure, there is provided a composition as described herein, wherein the composition is obtained by processing carrageenan or processed *Eucheuma* or semi refined carrageenan.

In an embodiment of the present disclosure, there is provided a composition as described herein, wherein the composition is obtained by processing carrageenan containing red seaweed. In another embodiment of the present disclosure, the carrageenan containing seaweed is selected from a group consisting of *Kappaphycus striatus, Eucheuma cottonii, Eucheurma denticulatum (spinosum) Halymenia durvillaea, Kappaphycus alvarezii, Chondrus crispus, Solieria chordalis, Porphyra purpurea, Euchuema isiforme, Hypnea musciformis, Solieria filiformis. Mastocarpus stellatus, Mastocarpus papillatus, Porphyra capensis, Furcerllaria* spp., *Gigartina* spp., *Gracillaria* spp., *Iridea* spp., *Anatheca* spp., *Meristotheca* spp., *Ahnfeltia* spp. *Gynmogongrus* spp. *Phyllophora* spp. and combinations thereof.

In an embodiment of the present disclosure, there is provided a composition as described herein, wherein the composition provides protection to plants against biotic stress.

In an embodiment of the present disclosure, there is provided a composition as described herein, wherein the composition is for use as plant defense pathway activator.

In an embodiment of the present disclosure, there is provided a process for preparing the composition comprising at least one sulphated galactose, said process comprising: (a) contacting a substance having a mixture of polysaccharides with water to obtain a slurry; and (b) depolymerizing the slurry by hydrolysis to obtain the composition. In another embodiment of the present disclosure, the substance is a solid biomass.

In an embodiment of the present disclosure, there is provided a process for preparing the composition comprising at least one sulphated galactose, said process comprising: (a) contacting a substance having a mixture of polysaccharides with water to obtain a slurry; and (b) depolymerizing the slurry by hydrolysis to obtain the composition, wherein the depolymerizing is done by using enzymatic hydrolysis in presence of at least one enzyme selected from a group consisting of cellulase, xylanase, mannase, sulphatase, anhydrogalactose dehydrogenase, α amylase, carrageenase, hydrolase, sulfurylase, and combinations thereof.

In an embodiment of the present disclosure, there is provided a process for preparing the composition as described herein, said process comprising: (a) contacting red seaweed with water to obtain to obtain a slurry with a total solid content in the range of 5-20%; (b) depolymerizing the slurry in a pH in a range of 1.0-4.0 at a temperature in a range of 50-180° C., and pressure in a range of 0.5-10 atmospheric pressure for a time in a range of 10 minutes-5 hours to obtain a hydrolysate; (c) optionally concentrating the hydrolysate to achieve a sugar concentration having Brix value in a range of 18-35 to obtain the composition or d) optionally drying it to obtain the powder composition.

In an embodiment of the present disclosure, there is provided a process for preparing the composition as described herein, said process comprising: (a) contacting carrageenan with water to obtain to obtain a slurry with a total solid content in the range of 5-20%; (b) depolymerizing the slurry in a pH in a range of 1.0-4.0 at a temperature in a range of 50-180° C., and pressure in a range of 0.5-10 atmospheric pressure for a time in a range of 10 minutes-5 hours to obtain a hydrolysate; (c) concentrating the hydrolysate to achieve a sugar concentration having Brix value in a range of 18-35 to obtain the composition in a liquid form or d) optionally drying the liquid form to obtain the composition in a powder form.

In an embodiment of the present disclosure, there is provided a use of the composition as described herein for the treatment of protection of plants.

In an embodiment of the present disclosure, there is provided a method for treating a plant, said method comprising: (a) obtaining the composition as described herein; and (b) contacting the composition with a plant or parts of a plant. In another embodiment of the present disclosure, the composition is contacted with the plant by a method selected from a group consisting of foliar application, soil application, seed treatment, injection onto plant tissues, and combinations thereof.

In an embodiment of the present disclosure, there is provided a method for treating a plant, said method comprising: (a) obtaining the composition as described herein; and (b) contacting the composition with a plant or parts of a plant, wherein the contacting composition comprises at least one sulphated galactose having a concentration of at least 10 mg/L with respect to the composition. In another embodiment, the composition comprises at least one sulphated galactose having a concentration in a range of 10 mg/L, to 500 mg/L with respect to the contacting composition. In yet another embodiment, the contacting composition comprises at least one sulphated galactose having a concentration in a range of 20 mg/L to 170 mg/L with respect to the contacting composition. In an alternate embodiment, the contacting composition comprises at least one sulphated galactose having a concentration in a range of 30 mg/L to 150 mg/L with respect to the contacting composition.

In an embodiment of the present disclosure, there is provided a method for treating a plant, said method comprising: (a) obtaining the composition as described herein; and (b) contacting the composition with a plant or parts of a plant, wherein the method comprises contacting the composition with the plant by foliar application, said foliar application comprises contacting the composition at a rate of 50-1000 ml/acre of crop. In another embodiment of the present disclosure, the foliar application is carried out in vegetative state of plant, and the application is done at 10-15 days after transplantation, subsequent application is done at an interval of 10-15 days till the onset of flowering and fruiting. In another embodiment of the present disclosure, the composition would be diluted and applied by drip application at the root zone of the plant In an embodiment of the present disclosure, there is provided a method of curing a plant, said method comprises treating the plant with a method as described herein.

In an embodiment of the present disclosure, there is provided a method of treating a plant as described herein, wherein treating is in combination with at least one penetrating agent. In another embodiment of the present disclosure, the at least one penetrating agent is selected from a group consisting of anionic surfactant, ionic surfactant, non-ionic surfactant, and combinations thereof. In yet another embodiment of the present disclosure, the at least one penetrating agent is selected from a group consisting of polysorbates, sodium dodecyl sulphate, lauryl dimethyl amine oxide, cetyltrimethylammonium bromide, polyethoxylated alcohols, polyoxyethylene sorbitan, octoxynol, N,N-dimethyldodecylamine-N-oxide, hexadecyltrimethylammonium bromide, polyoxyl 10 lauryl ether, Brij 721, bile salts, polyoxyl castor oil, nonylphenol ethoxylate, cyclodextrins, lecithin, methyl benzethonium chloride, and combinations thereof.

In an embodiment of the present disclosure, there is provided a method for treating a plant as described herein, wherein treatment is in combination with at least one bio-enhancer selected from a group consisting of seaweed extract, protein hydrolysates, humic acid, fulvic acid, microbial extracts, bio-fertilizer etc.

In an embodiment of the present disclosure, there is provided a method for treating a plant as described herein, wherein treating is in combination with at least one plant protective agent selected from a group consisting of fungicides, insecticides, microbial extracts, microbes including bacteria, fungi, viruses, bacteriophages etc.

In an embodiment of the present disclosure, there is provided a composition as described herein, wherein the composition is used for animal health protection.

In an embodiment of the present disclosure, there is provided a composition as described herein, wherein the composition is used as a plant defense pathway activator.

In an embodiment of the present disclosure, there is provided a composition as described herein, wherein the composition is used for curing animal.

In an embodiment of the present disclosure, there is provided a composition as described herein, wherein the composition is used for treating animal.

In an embodiment of the present disclosure, there is provided a composition as described herein, wherein the composition is used to protect plant from biotic stresses.

In an embodiment of the present disclosure, there is provided a composition as described herein, wherein the composition is used to protect plant from biotic stresses, and wherein the composition comprises at least one sulphated galactose having a concentration of at least 10 mg/L with respect to the composition which is contacted with the plant or parts of the plant.

In an embodiment of the present disclosure, there is provided a composition as described herein, wherein the composition is used to protect plant from abiotic stresses.

In an embodiment of the present disclosure, there is provided a composition as described herein, wherein the composition is used to protect plant from abiotic stresses, and wherein the composition comprises at least one sulphated galactose having a concentration of at least 10 mg/L with respect to the composition which is contacted with the plant or parts of the plant.

In an embodiment of the present disclosure, there is provided a composition as described herein, wherein the composition is used to protect plant from infections.

In an embodiment of the present disclosure, there is provided a composition as described herein, wherein the composition is used to protect plant from infections, and wherein the composition comprises at least one sulphated galactose having a concentration of at least 10 mg/L with respect to the contacting composition.

In an embodiment of the present disclosure, there is provided a method for treating an animal with the composition as described herein, said process comprising: (a) obtaining the composition as described herein; and (b) administering the composition with animal. In another embodiment of the present disclosure, administering comprises feed infusion, adding to the water used by the animal, topical application, and injecting the composition.

In an embodiment of the present disclosure, there is provided a method for treating an animal with the composition as described herein, said process comprising: (a) obtaining the composition as described herein; and (b) administering the composition with animal, wherein the composition comprises at least one sulphated galactose having a concentration of at least 10 mg/kg with respect to the feed being given to the animal. In another embodiment, the composition comprises at least one sulphated galactose having a concentration in a range of 10 mg/kg to 400 mg/kg with respect to the feed being given to the animal. In yet another embodiment, the composition comprises at least one sulphated galactose having a concentration in a range of 30 mg/kg to 300 mg/kg with respect to the feed being given to the animal. In an alternate embodiment, the composition comprises at least one sulphated galactose having a concentration in a range of 50 mg/kg to 200 mg/kg with respect to the feed being given to the animal.

In an embodiment of the present disclosure, there is provided a method for treating an animal with the composition as described herein, said process comprising: (a) obtaining the composition as described herein; and (b) administering the composition with animal, wherein the composition comprises at least one sulphated galactose having a concentration of at least 30 mg/tonne with respect to the culture water in which the animal is grown. In another embodiment, the composition comprises at least one sulphated galactose having a concentration in a range of 30 mg/tonne to 400 mg/tonne with respect to the culture water in which the animal is grown. In yet another embodiment, the composition comprises at least one sulphated galactose having a concentration in a range of 40 mg/tonne to 300 mg/tonne with respect to the culture water in which the animal is grown. In an alternate embodiment, the composition comprises at least one sulphated galactose having a concentration in a range of 50 mg/tonne to 200 mg/tonne with respect to the culture water in which the animal is grown.

In an embodiment of the present disclosure, there is provided a composition as described herein, wherein the composition further comprises at least one component selected from a group consisting of thickening agents, emulsifying agents, emulsifiers, stabilizers, suspending agents, and combinations thereof.

In an embodiment of the present disclosure, there is provided a use of sulphated galactose for protecting plants from infections.

In an embodiment of the present disclosure, there is provided a use of sulphated galactose for protecting plants from infections, wherein sulphated galactose is referred to any form of sulphated galactose as described herein.

In an embodiment of the present disclosure, there is provided a use of sulphated galactose for protecting plants from infections, wherein sulphated galactose is galactose-4-sulphate.

In an embodiment of the present disclosure, there is provided a use of sulphated galactose for protecting plants from infections, wherein sulphated galactose has a concentration of at least 10 mg/L In another embodiment, sulphated galactose has a concentration in a range of 10 mg/L-500 mg/L In yet another embodiment, sulphated galactose has a concentration in a range of 50 mg/L-400 mg/L In an alternate embodiment, sulphated galactose has a concentration in a range of 50 mg/L-300 mg/L In an embodiment of the present disclosure, there is provided a use of sulphated galactose for protecting plants from infections, wherein sulphated galactose has a concentration of at least 10 mg/L It can be contemplated that all the ranges above 10 mg/L Gal-S is intended to be considered as a disclosure for the use as described herein, concentration of Gal-S is in a range of 10 mg/L to 200 mg/L, or 20 mg/L to 180 mg/L, or 30 mg/L to 150 mg/L, or 40 mg/L to 140 mg/L, or 45 mg/L to 125 mg/L, or 75 mg/L to 120 mg/L In an embodiment of the present disclosure, them is provided a use of sulphated galactose for activating plant defense pathway.

In an embodiment of the present disclosure, there is provided a use of sulphated galactose for activating plant defense pathway, wherein sulphated galactose is referred to any form of sulphated galactose as described herein.

In an embodiment of the present disclosure, there is provided a use of sulphated galactose for activating plant defense pathway, wherein sulphated galactose is galactose-4-sulphate.

In an embodiment of the present disclosure, there is provided a use of sulphated galactose for activating plant defense pathway, wherein sulphated galactose has a concentration of at least 10 mg/L In another embodiment, sulphated galactose has a concentration in a range of 10 mg/L-500 mg/L In yet another embodiment, sulphated galactose has a concentration in a range of 50 mg/L-400 mg/L In an alternate embodiment, sulphated galactose has a concentration in a range of 50 mg/L-300 mg/L In an embodiment of the present disclosure, there is provided a use of sulphated galactose for activating plant defense pathway, wherein sulphated galactose has a concentration of at least 10 mg/L It can be contemplated that all the ranges above 10 mg/L Gal-S is intended to be considered as a disclosure for the use as described herein, concentration of Gal-S is in a range of 10 mg/L to 200 mg/L, or 20 mg/L to 180 mg/L, or 30 mg/L to 150 mg/L, or 40 mg/L to 140 mg/L, or 45 mg/L to 125 mg/L, or 75 mg/L to 120 mg/L In an embodiment of the present disclosure, there is provided a use of sulphated galactose for protecting animals from infections or abiotic stress.

In an embodiment of the present disclosure, there is provided a use of sulphated galactose for protecting animals from infections or abiotic stress, wherein sulphated galactose is referred to any form of sulphated galactose as described herein.

In an embodiment of the present disclosure, there is provided a use of sulphated galactose for protecting animals from infections or abiotic stress, wherein sulphated galactose is galactose-4-sulphate.

In an embodiment of the present disclosure, them is provided a use of sulphated galactose for protecting animals from infections or abiotic stress, wherein sulphated galactose has a concentration of at least 10 mg/kg of feed given to animal. In another embodiment, sulphated galactose has a concentration in a range of 10 mg/kg-500 mg/kg. In yet another embodiment, sulphated galactose has a concentration in a range of 50 mg/kg-400 mg/kg. In an alternate embodiment, sulphated galactose has a concentration in a range of 50 mg/kg-300 mg/kg.

In an embodiment of the present disclosure, there is provided a use of sulphated galactose for protecting animals from infections or abiotic stress, wherein sulphated galactose has a concentration of at least 10 mg/kg of the feed given to an animal. It can be contemplated that all the ranges above 10 mg/kg Gal-S is intended to be considered as a disclosure for the use as described herein, concentration of Gal-S can be in a range of 10 mg/kg to 500 mg/kg, or 20 mg/kg to 450 mg/kg, or 30 mg/kg to 420 mg/kg, or 40 mg/kg to 350 mg/kg, or, 50 mg/kg to 255 mg/kg, or 75 mg/kg to 215 mg/kg, or 100 mg/kg to 200 mg/kg, or 120 mg/kg to 200 mg/kg.

In an embodiment of the present disclosure, there is provided a use of sulphated galactose for treating infected plants.

In an embodiment of the present disclosure, there is provided a use of sulphated galactose for treating infected plants, wherein sulphated galactose is referred to any form of sulphated galactose as described herein.

In an embodiment of the present disclosure, there is provided a use of sulphated galactose for treating infected plants, wherein sulphated galactose is galactose-4-sulphate.

In an embodiment of the present disclosure, there is provided a use of sulphated galactose for treating infected plants, wherein sulphated galactose has a concentration of at least 10 mg/kg of the feed given to an animal. In another embodiment, sulphated galactose has a concentration in a range of 10 mg/kg-500 mg/kg. In yet another embodiment, sulphated galactose has a concentration in a range of 50 mg/kg-400 mg/kg. In an alternate embodiment, sulphated galactose has a concentration in a range of 50 mg/kg-300 mg/kg.

In an embodiment of the present disclosure, there is provided a use of sulphated galactose for treating infected plants, wherein sulphated galactose has a concentration of at least 10 mg/kg of the feed given to an animal. It can be contemplated that all the ranges above 10 mg/kg Gal-S is intended to be considered as a disclosure for the use as described herein, concentration of Gal-S is in a range of 10 mg kg to 200 mg/kg, or 20 mg/kg to 180 mg/kg, or 30 mg/kg to 150 mg/kg, or 40 mg/kg to 140 mg/kg, or 45 mg/kg to 125 mg/kg, or 75 mg/kg to 120 mg/kg.

In an embodiment of the present disclosure, there is provided a use of sulphated galactose for treating infected animals.

In an embodiment of the present disclosure, there is provided a use of sulphated galactose for treating infected animals, wherein sulphated galactose is referred to any form of sulphated galactose as described herein.

In an embodiment of the present disclosure, there is provided a use of sulphated galactose for treating infected animals, wherein sulphated galactose is galactose-4-sulphate.

In an embodiment of the present disclosure, there is provided a use of sulphated galactose for treating infected animals, wherein sulphated galactose has a concentration of at least 10 mg/kg of animal feed. In another embodiment, sulphated galactose has a concentration in a range of 10 mg/kg-500 mg/kg. In yet another embodiment, sulphated galactose has a concentration in a range of 50 mg/kg-400 mg/kg. In an alternate embodiment, sulphated galactose has a concentration in a range of 50 mg/kg-300 mg/kg.

In an embodiment of the present disclosure, there is provided a use of sulphated galactose for treating infected animals, wherein sulphated galactose has a concentration of at least 30 mg/tonne of culture water in which animal is grown. In another embodiment, sulphated galactose has a concentration in a range of 30 mg/tonne-500 mg/tonne. In yet another embodiment, sulphated galactose has a concentration in a range of 50 mg/tonne-400 mg/tonne. In an alternate embodiment, sulphated galactose has a concentration in a range of 100 mg/tonne-300 mg/tonne.

In an embodiment of the present disclosure, them is provided a use of sulphated galactose for stimulating animal immunity and stress tolerance.

In an embodiment of the present disclosure, there is provided a use of sulphated galactose for stimulating animal immunity and stress tolerance, wherein sulphated galactose is referred to any form of sulphated galactose as described herein.

In an embodiment of the present disclosure, there is provided a use of sulphated galactose for stimulating animal immunity and stress tolerance, wherein sulphated galactose is galactose-4-sulphate.

In an embodiment of the present disclosure, there is provided a use of sulphated galactose for stimulating animal immunity and stress tolerance, wherein sulphated galactose has a concentration of at least 10 mg/kg of animal feed. In another embodiment, sulphated galactose has a concentration in a range of 10 mg/kg-500 mg/kg. In yet another embodiment, sulphated galactose has a concentration in a range of 50 mg/kg-400 mg/kg. In an alternate embodiment, sulphated galactose has a concentration in a range of 50 mg/kg-300 mg/kg.

In an embodiment of the present disclosure, there is provided a use of sulphated galactose for stimulating animal immunity and stress tolerance, wherein sulphated galactose has a concentration of at least 30 mg/tonne of culture water in which animal is grown. In another embodiment, sulphated galactose has a concentration in a range of 30 mg/tonne-500 mg/tonne. In yet another embodiment, sulphated galactose has a concentration in a range of 50 mg/tonne-400 mg/tonne. In an alternate embodiment, sulphated galactose has a concentration in a range of 100 mg/tonne-300 mg/tonne.

Although the subject matter has been described in considerable detail with reference to certain examples and implementations thereof, other implementations are possible.

EXAMPLES

The disclosure will now be illustrated with working examples, which is intended to illustrate the working of disclosure and not intended to take restrictively to imply any limitations on the scope of the present disclosure. Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein. It is to be understood that this disclosure is not limited to particular methods, devices and experimental conditions described, as such methods and conditions may apply.

Working Examples

Example 1: Sclerotinia Infection in *Arabidopsis thaliana*

Figure 1:
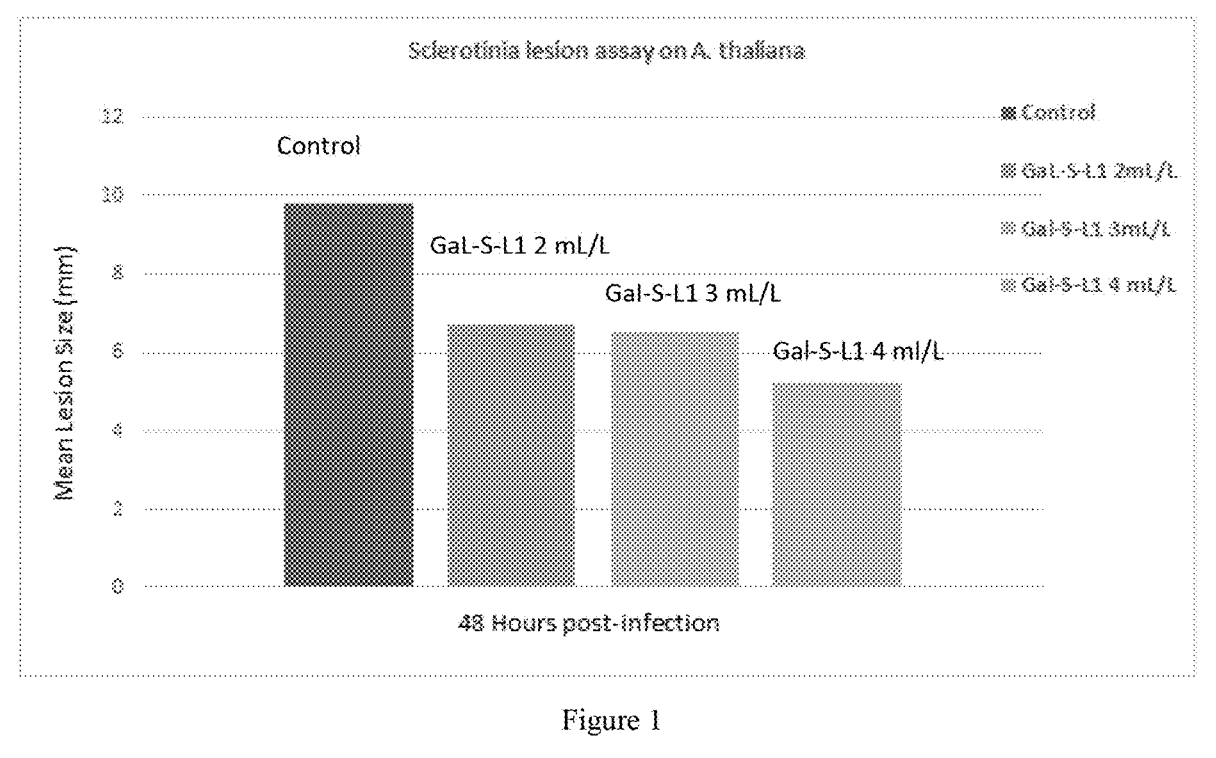

The present experiment was conducted with four treatments. The product used was a liquid formulation containing sulphated galactose (Gal-S, monosaccharide) as 20% of the total sugar component referred to as formulation. Gal-S-L1. Gal-S-L1 was diluted with water to reach the final concentrations of 2, 3, and 4 ml/L, for use as a foliar spray. Six plants were tested in each of the four groups (treatments and control). The model plant, *Arabidopsis thaliana* was grown on peat pellets and foliar sprayed with the aforesaid diluted products (or water as control)24 hours prior to infection with the pathogen. 24 hours post-treatment, each plant was infected equally with the fungus *Sclerotinia* sp. on two separate leaves. The area of lesion surrounding the infection spot was measured using a vernier caliper 48 hours post-infection. FIG. 1 of the present disclosure illustrates in the treatment groups compared to the untreated control group that the lesions caused by pathogen were lesser by about 44% when compared to the untreated control (refer, FIG. 1). The present disclosure thus discloses a monosaccharide sulphated galactose-based formulation, treatment with which could effectively control the spread of a fungal pathogen when applied onto the plant.

Example 2: *Alternaria solani* Infection Scoring Assay in Tomato Plants

Figure 2:
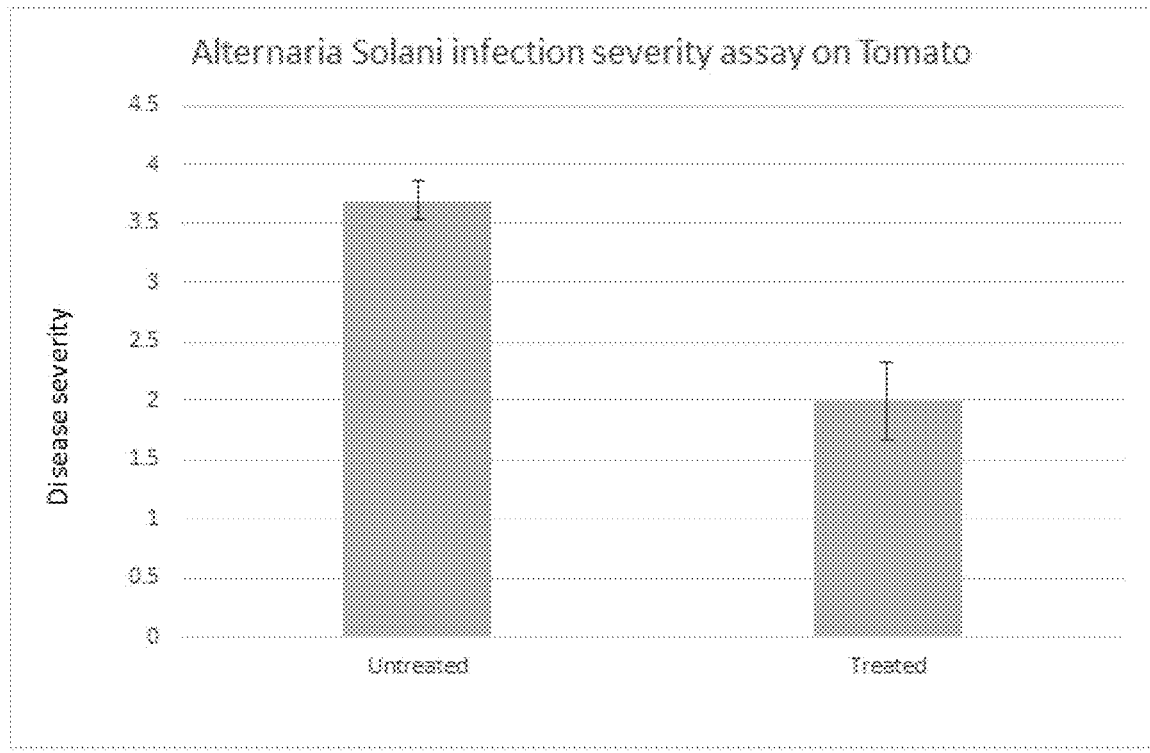

The present experiment was conducted with two treatments. The product used was a liquid formulation containing Gal-S referred to as formulation Gal-S-1. Gal-S-L1 was diluted with water (final concentration of 4 mL/L) for use as a foliar spray. The diluted product (4 mL/L) and a control (water) were used on six tomato plants per group. Tomato plants grown in pots were sprayed with the diluted Gal-S-L1 formulation (or water for control) 24 hours prior to infection. Upon which, each plant was infected equally with *A. solani* spores ($2\times10^3$ per mL) on whole foliage. To maintain the ambient humidity, all plants were covered in transparent polythene covers and allowed to grow for one week. The severity of the infection was scored using 0-5 rating scale (Pandey et al., (2003), 364-371). Clearly the severity of the symptoms was about 50% lower in Gal-S-L1 treated group (refer, FIG. 2) when compared to the plants of the untreated group. Thus, it was demonstrated that the Gal-S-L1 formulation could control the growth of a fungal pathogen and provides protection to the plant.

Example 3: Comparative Field Trial with Fungicide on Tomato Crop

Figure 3:
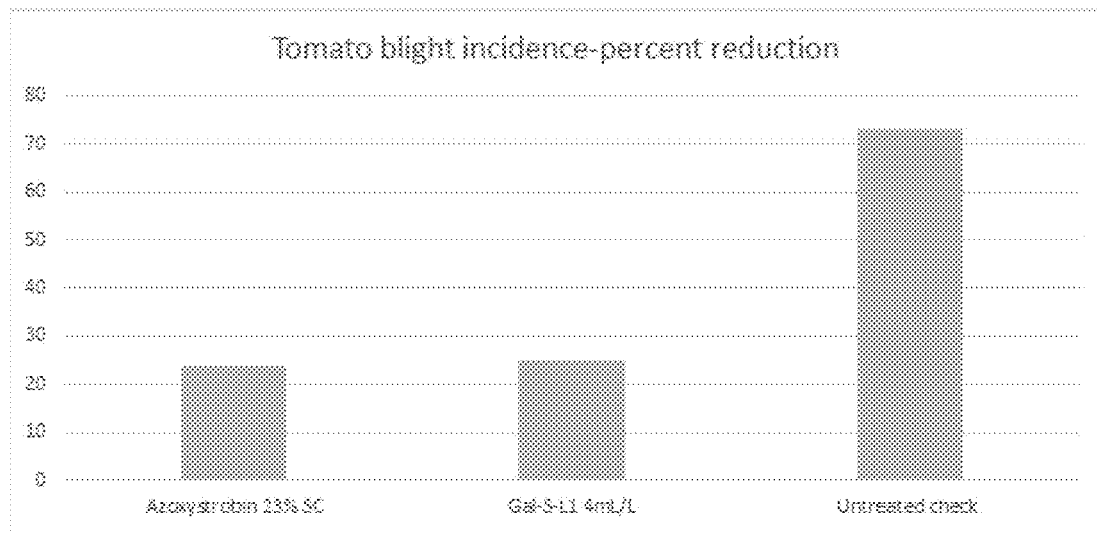

The present experiment demonstrates a field trial experiment which was conducted on a tomato crop. In this experiment, Gal-S-L1 was sprayed at 2 mL/L dilution, while for comparison, a commercially available chemical fungicide containing azoxystrobin 23% SC was used at 1.0 mL/L dilution and compared to a control group wherein water was sprayed for comparison. All the treatments were given as foliar spray, first spray was conducted about 15 days after planting tomato seedlings in the field, followed by two more sprays with 15 days interval between each spray. The tomato plants in each group were ensured with equal supply of water and regular nutrients through the application of farmyard manure (FYM). Fungal disease incidence (Tomato blight) was recorded at the completion of all the sprays. The results in FIG. 3 clearly show the Gal-S-L1 is quite effective in controlling the disease incidence. This clearly showed the plant protective effect of Gal-S-IL1, is in a range that is comparable to the effect of a commercial fungicide.

Figure 4:
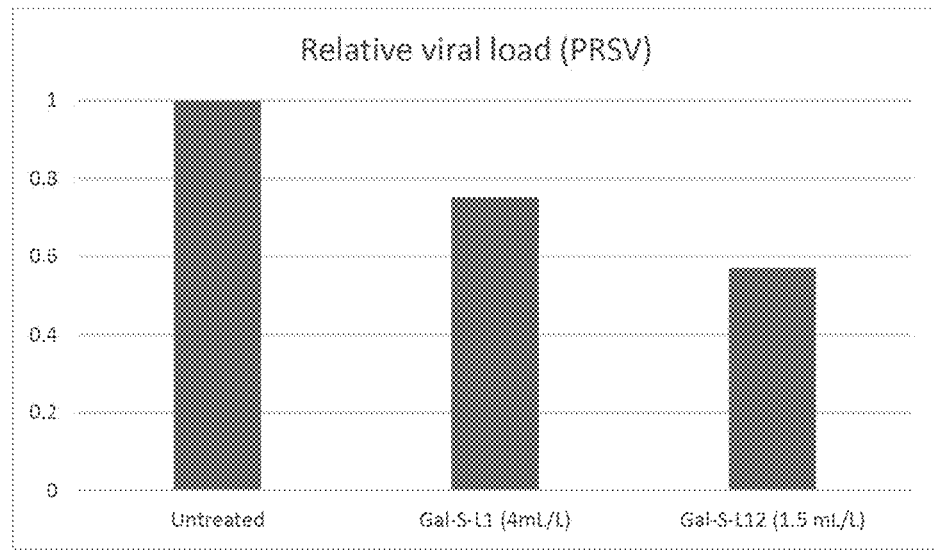

Example 4: qPCR-Based Assay to Show Reduction in Viral Load of Papaya Ring Spot Virus (PRSV) in Papaya Crop The present experiment used liquid formulations containing different levels of Gal-S, referred to as formulation Gal-S-L1 and Gal-S-L12. For one group of plants, Formulation Gal-S-L12 (containing Gal-S at 89% of the total sugar) was used at a dose of 1.5 ml/L, accounting for Gal-S concentration of about 128 mg/L, while another group was treated with Formulation Gal-S-L1 containing Gal-S at 20% of the total sugar, accounting for Gal-S concentration of about 56 mg/L The $3^{rd}$ group of plants was treated only with water. The experiment comprised three groups of plants; i.e plants infected with PRSV and treated with Gal-S-L1, plants infected with PRSV & treated with Gal-S-L12 and a third group of plants that was infected with PRSV and left untreated, with six papaya plants in each group (age of papaya plants was about 60 days). The treated group of plants received product treatment (either Gal-S-L12 or Gal-S-L1) while untreated group received water a) before PRSV sap (Bau et al., (2003), 112-120) inoculation, b) 24 hrs after sap inoculation and c) 1 week after sap inoculation. The leaf samples were collected from each group before sap inoculation and 10 days after sap inoculation. All the leaf samples were stored at −80° C. till further analysis. In this experiment a set of primers specific to amplify the PRSV NiB gene were used in a SYBR green based quantitative Polymerase Chain Reaction (qPCR). 5' AGTCGGCCCGAAGCAAT-TTT 3' (SEQ ID NO: 1) and 5'CTCATCACACTCAAGA-TAGTCCTGAA3'(SEQ ID NO:2) primer sequence were used respectively, as forward and reverse primers to amplify PRSV NiB gene specifically. Total RNA was isolated from leaf sample, cDNA was prepared by using reverse transcriptase reaction before analyzing by qPCR. Based on the Ct values, fold change of viral NiB gene was calculated. Compared to the untreated group, both Gal-S-L1 and the Gal-S-L12 treated group showed reduction in PRSV load (refer, FIG. 4) with the Gal-S-L12 performing better than the Gal-S-L1 implying that the treatment with product indeed inhibited PRSV multiplication in host plant cells. The results also clearly demonstrate that the virus load was much lower with increase in Gal-S content in the liquid formulations thus showing the importance of Gal-S concentrations in plant protective effects.

Figure 5:
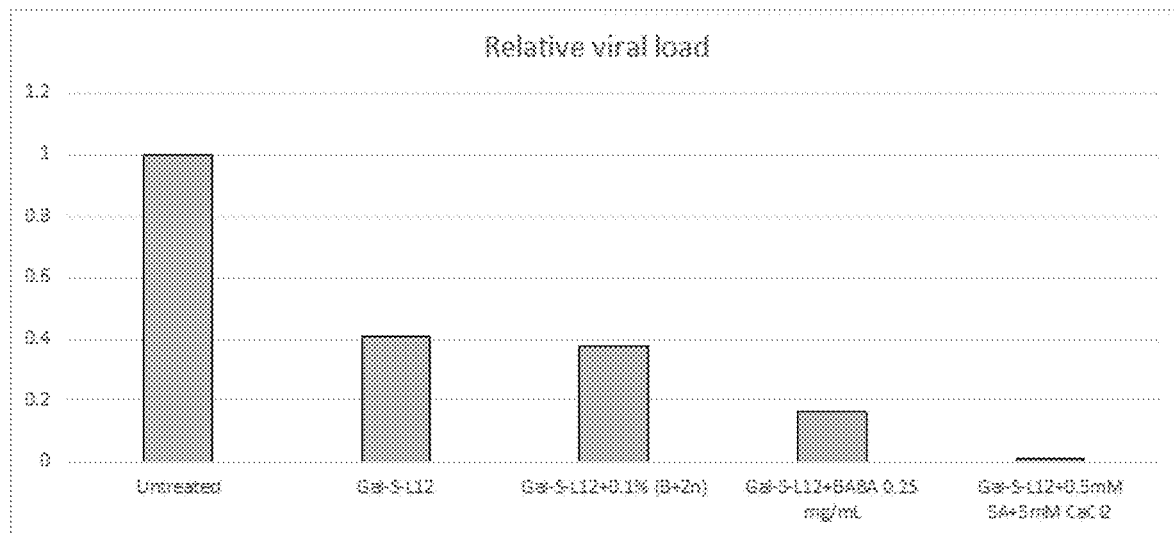

Example 5: Improved Efficacy of Monosaccharide Sulphated Galactose-Based Composition with Additives The present experiment was conducted as in Example 4 but the product (Gal-S-L12) was formulated with metal ions (Boron (0.1%) and Zinc (0.1%)) or with salicylic acid (0.5 mM) and $CaCl_2$ (3 mM) or with beta aminobutyric acid (0.25 mg/ml) before treating on plants. A clear reduction in relative viral load of the pathogen PRSV (refer, FIG. 5) was noticed for these improved formulations. |001681 Thus, it was established that a combination of the preparations rich in galactose sulphate monosaccharide along with metal ions and salicylic acid or amino acids such as beta aminobutyric acid improved the response far more than any of them alone.

Example 6: Preparation of Carrageenan Containing Raw Material for Manufacture of Gal-S Formulation Preparation from the Red Seaweed *Kappaphycus striatus*

1 kg of fresh *Kappaphycus striatus* (sacol) seaweed was sourced from Bali island in Indonesia and processed through a kitchen juicer equipped with a rotating screw press and a perforated bowl. Whole seaweed was brought into contact with the rotating screw which breaks it into small pieces. The screw press squeezed the seaweed pieces against the perforated bowl and was immediately separated into juice and juice extracted pulp without forming intermediate slurry. The seaweed juice extracted pulp and the seaweed juice were collected separately in a continuous manner from two different outlets of the equipment. The amount of juice extracted pulp collected was 350 g and the amount of juice collected was 650 g. The moisture content of the juice extracted pulp was 80% and the Brix of the juice was 5%. The juice extracted pulp thus obtained was further dried in a hot air oven to get the dried seaweed flakes (moisture content approximately 10%). The juice extracted pulp (80%) moisture or the dried seaweed flakes may be used as the starting material for the manufacture of sulphated galactose (Gal-S) formulations.

Alternatively, dried seaweed flakes could also be prepared by taking fresh *Kappaphycus striatus* seaweed and drying it directly either under sunlight or in a hot air oven to a moisture content of (approximately 10%). The dried seaweed are then chipped into smaller pieces to obtain dried seaweed flakes as for use as a raw material for the manufacture of Gal-S Formulation.

Example 7: Preparation of Gal-S Formulations from Dried Seaweed Flakes

The process for preparing the composition as described herein, comprises the following steps:
  a. The dried seaweed flakes (10% moisture content) obtained as described above were slurried with water to a final suspended concentration of 10% weight by weight (w/w). The pH of the suspension was adjusted to approximately pH 2.4 using an acid catalyst. An aliquot of this suspension was centrifuged and set aside as a "zero-hour sample"
  b. The above reaction mixture was heated and held at a temperature range of 119-123° C. and at 1 bar pressure under constant stirring conditions.
  c. The reaction was allowed to proceed for 2.5 hours. A sample was withdrawn at 1 hour and 2.5 hours for analytical purposes. At the end of 2.5 hours, the mixture was cooled to room temperature to stop the reaction.
  d. A part of the samples were centrifuged, and the supernatant was concentrated to obtain liquid Gal-S formulations. Another part of the sample was dried before or after centrifugation to obtain powder Gal-S formulations. The liquid Gal-S formulations were analyzed for quantifying the total sugars using the anthrone sulfuric acid method (as outlined in the example below) and for the concentration of Gal-S by HPLC-MS (as outlined in the example below) after subtracting the corresponding values for the "zero-hour" samples.
  e. The percentage of Gal-S as a proportion of the total sugars was calculated using the above values. The results are shown below in Table 1. Overall, the examples section provides working and non-working examples with respect to the ingredients used in the present composition. Also, the process as described in the present section is only one method for preparing the composition, other methods for preparing the same can be contemplated.

TABLE 1

Percent saccharide composition post-hydrolysis with time (hr)

| Time | Total Sugar (in mg/ml) | Monosaccharide % Galactose-4-sulphate (Gal-S) | Disaccharide % Carrabiose | Trisaccharide % Carratriose | HMF | Formulation Name |
|---|---|---|---|---|---|---|
| 1.0 hr | 69.06 | 20.2% | 1.12% | 27.23% | 6.4% | Gal-S-L1 |
| 2.5 hr | 96.35 | 88.6% | 0.04% | 5.24% | 16.1% | Gal-S-L12 |

Example 8: Procedure for Analysis of Gal-S Formulations by HPLC-MS for Gal-S Concentration Mass spectrometric analysis of the samples was carried out on an Agilent 6460 triple quadrupole instrument, equipped with an electrospray ionization source and an online UPLC system (Agilent 1290 Infinity). The sugars were analyzed in negative ion mode, while HMF was analyzed in the positive ion mode. For sugar analysis, an XBridge amide HPLC column was used with an acetonitrile and water gradient. For HMF analysis, an Agilent Eclipse C18 column was used with methanol and water (containing 0.1% Formic acid) gradient. The samples were diluted in MQ water prior to injection. Mass analysis was carried out in MRM (multiple reaction monitoring) mode, resulting in precursor and daughter ion spectra. The standard curves for all the compounds were constructed between 5 to 200 ppb. The sugar standards. i.e. carrabiose sodium salt, kappa carratriose sodium salt, D-Galactose-4-O-sulphate sodium Salt) were purchased from Carbosyth, UK. HMF was purchased from Sigma Aldrich.

Example 9: Method for Measurement of Total Sugars in Gal-S Formulations Using the Anthrone Sulfuric Acid Method The process for measurement of total sugars where the samples obtained from the hydrolysis process as described above in Example 7, step (d), were analyzed for total sugar content using anthrone sulfuric acid method. In the case of powder samples, the product is dissolved in water and centrifuged and the supernatant is used for the analysis. In this method, 0.1 g anthrone (Himedia Cat no. GRM314) is dissolved in 100 ml of concentrated sulfuric acid solution. Glucose standard solution of 0.25 g/l was prepared. A series of Glucose standard solutions 0, 0.05, 0.1, 0.15, 0.2 and 0.25 g/l were prepared by adding required amount of water, 0.4 ml of standard solutions or sample was added to 0.8 ml of anthrone solution and the reaction mixture was incubated at 4° C. for 10 min followed by 95° C. for 20 min. The reaction mixture was cooled down to room temperature for 10-15 minutes and absorbance of the solution was measured at 620 nm using a Spectrophotometer.

Example 10: Additional Methods for Obtaining the Composition of the Present Disclosure and Possible Mixtures of Sulphated Galactose that can be Obtained Preparations rich in galactose sulphate (Gal-S) may be manufactured from starting materials such as carrageenan or carrageenan containing materials like red seaweeds. Examples of such seaweeds are *Kappaphycus striatus, Eucheuma cottonii, Eucheuma denticulatum (spinosum.) Halymenia durvillaea, Kappaphycus alvarezii, Chondrus crispus, Solieria chordalis, Porphyra pupurea, Eucheuma isiforme, Hypnea musciformis, Solieria filiformis, Mastocarpus stellates, Mastocarpus papillatus, Porphyra capensis, Furcerllaria* spp., *Gigartina* spp, *Gracillaria* spp., *Iridea* spp., *Anatheca* spp., *Meristotheca* spp., *Ahnfeltia* spp. *Gynmogongrus* spp. *Phyllophora* spp. and combinations thereof.

The starting material is subjected to controlled hydrolysis (example with acids at temperatures between 120-150° C. for a time period between 15 minutes to 5 hours) to cause the breakdown of the polysaccharide backbone to the desired extent. The hydrolysis may be controlled by varying hydrolysis temperature and time conditions as well as the concentration of the hydrolysing agent (acid, peroxide, alkali etc.) carefully to allow sufficient breakdown to happen. At the same time, very excessive hydrolysis can result in the removal of the sulphate that is linked to the sugar resulting in only galactose. The extent of the hydrolysis may be measured using HPLC linked to Mass spectrometry (MS). In addition, a precise control of the hydrolysis may be achieved by using a continuous hydrolysis equipment. The carrageenan may be any carrageenan like kappa carrageenan, iota carrageenan or lambda or hybrid carrageenan. Depending upon the carrageenan used the galactose sulphate so obtained may be sulphated in mom than one position on the galactose moiety. For example, preparations rich in galactose sulphate (Gal-S) made from lambda carrageenan will produce the mixture of the monosaccharide Galactose sulphate which is sulphated in one place as well as two places on the galactose moiety.

Within the range of conditions for hydrolysis of seaweed biomass as disclosed in the invention by Nori et al U.S. Pat. No. 10,358,391 B1, (also an author of this instant disclosure) it was found that while most of the hydrolysates produced under these conditions could act as plant biostimulants when used in accordance with the teachings of Nori et al, surprisingly, only a certain subset of hydrolysates which were produced under extreme conditions of hydrolysis (e.g. higher temperatures like 95 deg C. with holding times between 4 to 12 hours or at 120 deg C. to 150 deg C. and holding times between 5 hours to 15 min, yielded hydrolysate mixtures that were capable of strong plant and animal protective effects as being disclosed in the present disclosure.

Upon analysis of such protective hydrolysate mixtures using HPLC-mass spectrometric techniques it was found that a significant fraction of the hydrolysate (i.e. more than 15% of the total sugars) was present as sulphated galactose (e.g mono-sulphated galactose and di-sulphated galactose) all of which are less than 400 Da molecular weight. The formation of this range of molecular weights during the hydrolysis process has not been previously mentioned in the invention by Nori et al.

When two such hydrolysate mixtures of differing sulphated galactose content were compared, tt was also surprisingly found that that the higher the content of sulphated galactose in the mixture, the more potent the protective effect. This relationship between the concentration of the sulphated galactose content and the plant and animal protective effect of the galactose sulphate containing mixture is a non-obvious feature of the present disclosure.

It was also found, especially in the case of hydrolysis using extreme conditions, that a significant amount of hydroxy methyl furfural was formed (exceeding 2% of the total amount of sugars in the formulation). Hydroxymethyl furfural is a derivative of monosaccharide and is easily formed from the saccharide, anhydrogalactose under conditions of temperature and acidity (though it is formed from other saccharides as well). The saccharide, anhydrogalactose is a constituent of carrageenan. Thus, hydroxymethyl furfural may be also considered as an additional marker of the unique hydrolysate mixtures produced using certain processes of manufacture which also result in elevated levels of sulphated galactose that have plant and animal protective effects. It was also found as shown in example 14 that hydroxymethyl furfural could independently have protective effects on plants. This is a surprising and new finding which has not been reported before and therefore a hydrolysate mixture of galactose sulphate and saccharides which is independently plant protective may be enhanced by the formation of hydroxymethyl furfural which is formed using certain processes of manufacture. It may be noted here that hydroxy-methyl furfural may not always be formed when using other methods of manufacture that use enzymatic hydrolysis or peroxide hydrolysis but may be formed in process that use ionic liquids as a hydrolysis medium.

Still other methods of preparing compositions rich in galactose sulphate is to use ionic liquids, peroxides than can break down carrageenan containing materials to saccharides and galactose sulphate under suitable conditions.

Depending upon the carrageenan used, the galactose sulphate may be sulphated in more than one position on the galactose moiety. For example, preparations rich in galactose sulphate (Gal-S) made from lambda carrageenan will produce the mixture of the monosaccharide Galactose-2-O-sulphate and Galactose-2,6-di-sulphate which is sulphated in one place as well as two places respectively, on the galactose moiety. On the other hand, if the preparation is made from kappa or iota carrageenan then the main monosaccharide moiety would be Galactose-4-O-sulphate. If the starting raw material is mixture of carrageenans then the main monosaccharide upon hydrolysis would be a mixture of Galactose-2-O-sulphate, Galactose-4-O-sulphate and Galactose-6-O-sulphates.

Possible raw materials that can be construed as a part of the present disclosure: kappa-carrageenan (polymer of the repeating unit β-D-Galactose-4-O-sulphate-α-3,6-Anhydro-D-Galactose), precursor of kappa-carrageenan (polymer of the repeating unit β-D-Galactose-4-O-sulphate-α-D-Galactose-6-O-sulphate), iota-carrageenan (polymer of the repeating unit β-D-Galactose-4-O-sulphate-α-3,6-Anhydro-D-Galactose-2-O-sulphate), precursor of iota-carrageenan (polymer of the repeating unit β-D)-Galactose-4-O-sulphate-α-D-Galactose-2,6-O-disulphate), lambda carrageenan (polymer of the repeating unit β-D-Galactose-2-O-sulphate-α-D-Galactose-2,6-O-disulphate), and mixtures of lambda and kappa-carrageenans are also possible in some seaweeds.

Some of the representative structures of sulphated galactose are presented below:
1. D-galactose-4-O-sulphate (CAS ID: 125113-68-0 tor the sodium salt)

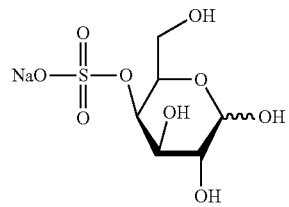

2. D-galactose-6-O)-sulphate (CAS ID: 125455-62-1 for the sodium salt)

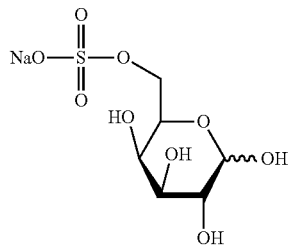

Other methods of making preparations rich in galactose sulphate include the use of enzymes that can break down carrageenan to galactose sulphate optionally followed by acid hydrolysis. Examples of such enzymes used singly or in combination depending upon the carrageenan containing raw material are cellulase, xylanase, mannanase, sulphatase, anhydrogalactose dehydrogenase, α-amylase, carrageenase, hydrolase, sulfurylase (refer, Seaweed Hydrocolloid Production: An Update on Enzyme Assisted Extraction and Modification Technologies).

Example 11: Preparations Rich in Galactose Sulphate May Also be Obtained by Chemically Synthesizing them Preparations rich in galactose sulphate may also be obtained by chemically synthesizing them as described by Peat S et. al., 1960. (Sulfates of monosaccharides and their derivatives. Part 1. Preparation. J. Chem. Soc. 4761-4766) or by Turvey et. al., 1962 (407. Sulphates of monosaccharides and derivatives. Part IV. Galactose 4-sulphate. Journal of the Chemical Society (Resumed), 2119)

Chemical synthesis of Galactose-4-O-sulphate was carried out starting from Methyl alpha-D-galactopyranoside by the following steps
  a. 1.4 g of Methyl alpha-D-galactopyranoside was dissolved in dry pyridine (45 ml.) and the mixture was cooled to −40'C. To this precooled mixture, 3.39 ml of benzoylchloride was added dropwise using a syringe. The reaction was carried out for 2 hours at −40° C. post which the reaction mixture was left in an ice bath overnight. Pyridine was evaporated and the reaction mixture was dissolved in chloroform (25-30 mi). The organic layer was washed with 1) dilute HCl, 2) 5% aq. NaHCO$_3$ and finally with water. The organic layer was collected and dried over anhydrous MgSCO4. The organic layer was evaporated and the product (Methyl 2,3,6-tri-0-benzoyl-α-D-galactopyranoside) was obtained by crystallizing with ethanol b. 1 g of Methyl 2.3,6-tri-0-benzoyl-α-D-galactopyranoside was dissolved in dry pyridine (12 mL) and the mixture stirred at room temperature. To this mixture, 960 mg of Pyr·SO3 was added and reaction mixture was maintained under reflux conditions for 3 hours at 65° C. The reaction mixture was cooled to room temperature and residual pyridine was removed. 25 ml of Dichloromethane was added to the mixture and the organic layer was washed with dilute NaHCO$_3$(5% w/w solution). The organic layer was collected and dried on anhydrous MgSO4. The filtrate was evaporated on vacuum to result in a pale yellow oil that was purified using flash chromatography to obtain Methyl 2,3,6-tri-0-benzoyl-α-D-galactopyranoside-4-sulfate c. 0.9 g of Methyl 2,3,6-tri-0-benzoyl-α-D-galactopyranoside-4-sulfate was dissolved in dry methanol (30 mL) and the mixture stirred at room temperature. 7.5 ml of NaOMe was added to this and reaction was stirred overnight at room temperature the reaction was monitored. The reaction mixture was pH neutralized and evaporated to remove solvent. The crude product (Methyl Galactose-4-O-sulphate) was purified on a column with 30%0 methanol in DCM, 100% Methanol wash d. 700 mg of Methyl Galactose-4-O-sulphate was added to 3 ml of dry dichloromethane and 840 mg of trityl tetrafluoroborate under nitrogen atmosphere. The reaction mixture was stirred at room temperature overnight and quenched with an excess of sodium hydrogen carbonate. The organic phase was washed with water, however, the product moved to aqueous layer along with NaHCO$_3$. The aqueous layers were collected and concentrated under vacuum and methanol was added to precipitate sodium hydrogen carbonate. Gal-S precipitated in the methanol fraction and the crude solid fraction was mixed with acetic acid. The mixture was column purified with 100% Methanol solvent running phase and the fractions containing Gal-S were collected and concentrated under vacuum to obtain dry powder.

The composition of dry powder was evaluated by performing HPLC-MS (as described in example 8) and presence of Galactose-4-O-sulphate was confirmed.

Example 12: Effect of the Composition for Protecting and Curing Animals from Diseases The composition of the present disclosure can also be used for protecting and curing animal from various diseases like bacterial and viral disease.

The composition of the present disclosure can also be used for protecting the animal from various abiotic stresses like temperature and salinity.

The composition of the present disclosure can also be applied directly to a water body in which the aquatic animals are grown (nursery stage) to stimulate the defense pathways.

Optionally, the composition can be fed to *Artemia* (crustacean feed for shrimp), and the enriched *Artemia* can be fed to the shrimp as feed.

The composition can be diluted in water to form a homogenous solution and then mixed in the feed and then fed to the aquatic animals (fish and shrimp) to stimulate the defense pathways. The application is to be applied in a prophylactic manner but can also be applied after the disease onset.

The preparations rich in galactose sulphate can also be converted into powder formulations and can be mixed with the feed at appropriate dilutions and fed to livestock, birds and other animals.

Figure 6:
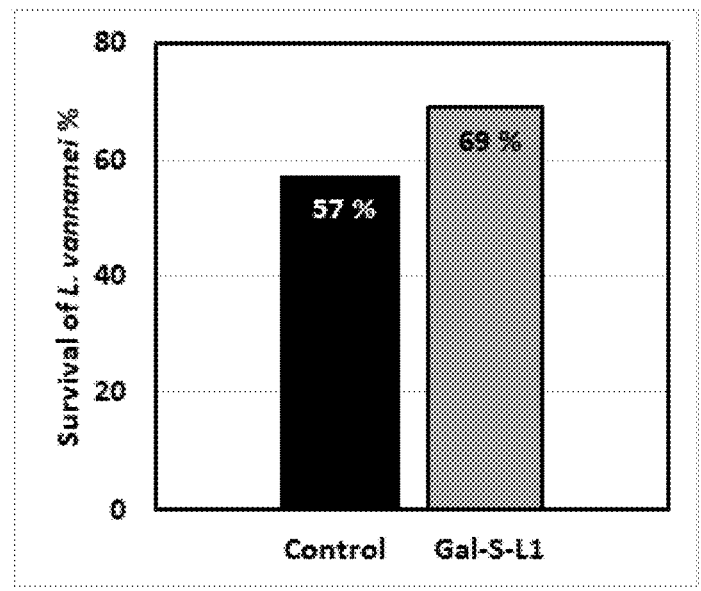

One of the examples of the use of composition is shown below:

A) Example 12A: Post larvae (PI 1) of the shrimp *L. vannamei* were stocked at a density of 60 shrimp/sq·m, in four plastic lined outdoor ponds of 300 sq·m each. The salinity of the water was 36-39 ppt. The pH of the water was in the range of 7.6-8.2. Aeration was provided using paddle wheel aerators to maintain sufficient dissolved oxygen levels. The feeding was carried out four times a day, and the cultivation was carried out for a period of about 110 days. The shrimp in the control ponds (2 replicates) were fed with commercial diet for the entire duration. Shrimp in the treated ponds (2 replicates) were fed with commercial diet premixed with Gal-S-L1 at an effective dosage of 5 g/kg feed for two alternate weeks during the second month of the cultivation. For the rest of the cultivation period, the treated ponds received the commercial diet similar to that of the control. The final average body weight of the shrimp across all ponds was about 20 g. The shrimp were harvested and weighed, and the number of survived shrimp was estimated from the control and treated ponds. FIG. 6 shows that the survival of the fully-grown shrimp was higher for the ponds which included a two-week diet of Gal-S-L premixed feed compared to control. In the present Example, the Gal-S-L1 that was fed to shrimps had an effective dosage of 60 mg/kg of Gal-S which was shown to improve the survival of shrimp.

Figure 14:
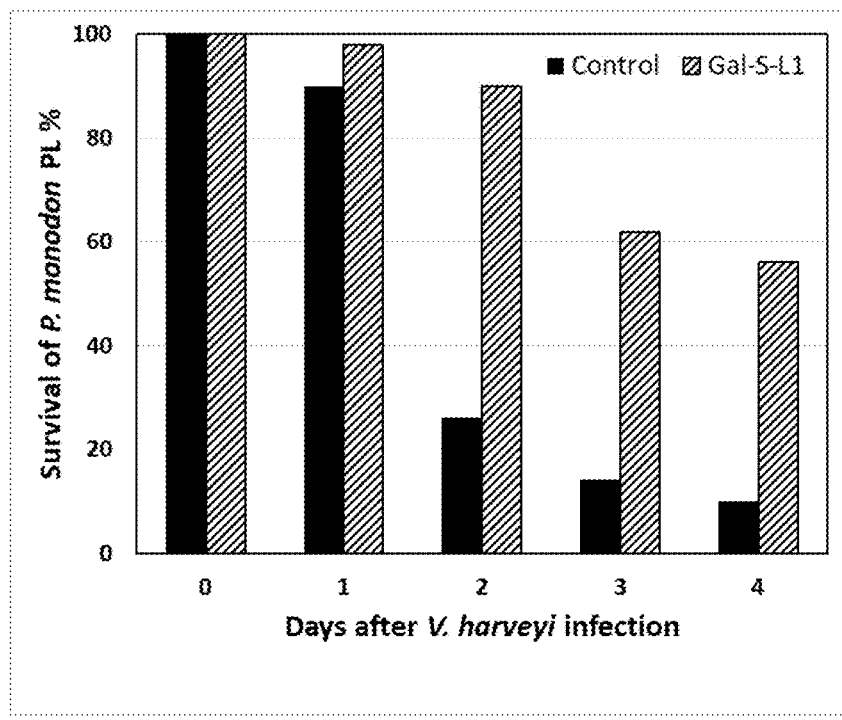
FIG. 14 illustrates the increase in survival of *P. monodon* post larvae (PL) in Gal-S-L1 treated shrimp relative to control, after a *V. harveyi* bacterial disease challenge thus showing the ability of Gal-S containing formulation to protect the animal from disease in accordance with an embodiment of the present disclosure.

Another example of the use of the Gal-S compositions is given below:

B) Example 12B: Gal-S-L1 Treatment Increases the Survival and Tolerance to Bacterial Infection in *P. monodon* Post Larvae (PL) Shrimp Shrimp larval culture was set-up in a hatchery in 100 L tanks in which 10000 larvae (Nauplius 1 or N1) were stocked in each tank. The experiment was conducted from N1 to PL10 stages and the shrimp were fed with *Artemia salina*. Gal-S-L1 was administered at a dosage of 0.003 ml/L of water per day in the treated tank while the control tank did not receive any Gal-S-L1. 50 PL10 shrimp from each from the control and treated tanks were collected and divided into two replicates having 25 PL each. The control and treated PL 10 were infected with *V. harveyi* (LB3) in water at a dose of 1×10^6 cfu/mL and the percentage survival were recorded daily up to four days post infection. FIG. 14 shows that the survival in the presence of bacterial disease remains high when the shrimp were treated with Gal-S-L1. In the present Example, the administered dosage of 0.003 ml/L of Gal-S-L1 had an effective dosage of Gal-S as 30 mg Gal-S/tonne of culture water was shown to improve survival of the shrimp post larvae.

Example 13—Detached Tomato Leaf Assay on Tomato Crop Shows Improved Efficacy with Compositions Containing a Higher Percentage of Gal-S while Total Sugar Concentrations being Similar Preparation of *Alternaria solani* fungal spores: *Alternaria solani* was cultured on PDA plates and allowed to grow for about a week at 30° C. Fully grown areal mycelium was removed using a sterile brush and the fungal mat grown on surface of agar was cut into small pieces and placed on plates containing sucrose-agar sporulating medium. Plates were further incubated at 30° C. in dark for 3-4 days upon which spores were collected by adding 0.1% tween 20 and number of spores were counted under a microscope.

Figure 7:
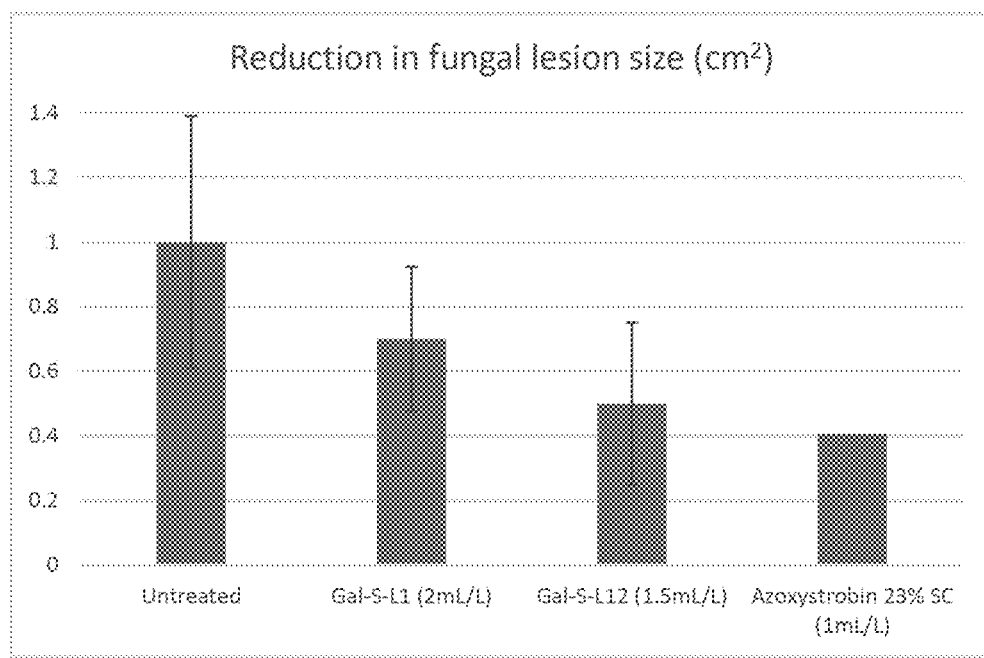

Detached tomato leaf Antifungal assay: In this assay, Antifungal efficacy of the Gal-S-L1 and Gal-S-L12 were compared by measuring the damage/lesion size due to fungus inoculation on detached tomato leaf. Briefly, about 30-40 days old tomato seedlings were first sprayed with appropriate dilution of the product formulations (i.e 2 ml/L of Gal-S-L1 formulation providing a total sugar concentration of approximately 140 mg/ml out of which Gal-S concentration was approximately 28 mg/l and 1.5 ml/L of Gal-S-L12 providing a total sugar concentration of approximately 140 mg/L out of which Gal-S concentration was 128 mg/L of Gal-S), while the untreated control and healthy group of plants were treated only with water. 48 hrs after treatment, four leaves from each of the plant (typically $2^{nd}$ and $3^{rd}$ tier from the top) were detached and surface sterilized by washing in 1% sodium hypochlorite solution followed by 70% ethanol and in sterile water for 1 min. The petiole of all the leaves were covered with moist cotton plug and placed on a sterile filter paper that is kept in a sterile petri plate. Further, the tomato leaves were inoculated by spotting 5 μL of spore suspension containing *Alternaria solani* spores (typically at a concentration of 10^4 spores per mL) at the middle of the sterile leaf lamina followed by incubation in dark at room temperature for 2 weeks. 12 days after inoculation, all the leaves were scanned using WinFO-LIA™ software to record the size of fungal lesion size. The results (FIG. 7) showed that the size of the fungus-induced lesion/damage was lower in the leaves treated with Gal-S-L12 at 1.5 ml/L than in the leaves treated with Gal-S-L1 at 2 ml/L. Since both the treatments had a similar total sugar concentration but the treatment with Gal-S-L12 had a higher Gal-S concentration, it is clear that Gal-S plays an important role in activating plant protective effects leading to reduction in the size of fungal lesions.

Example 14: Plant Protective Effects of Gal-S and HMF

Figure 8:
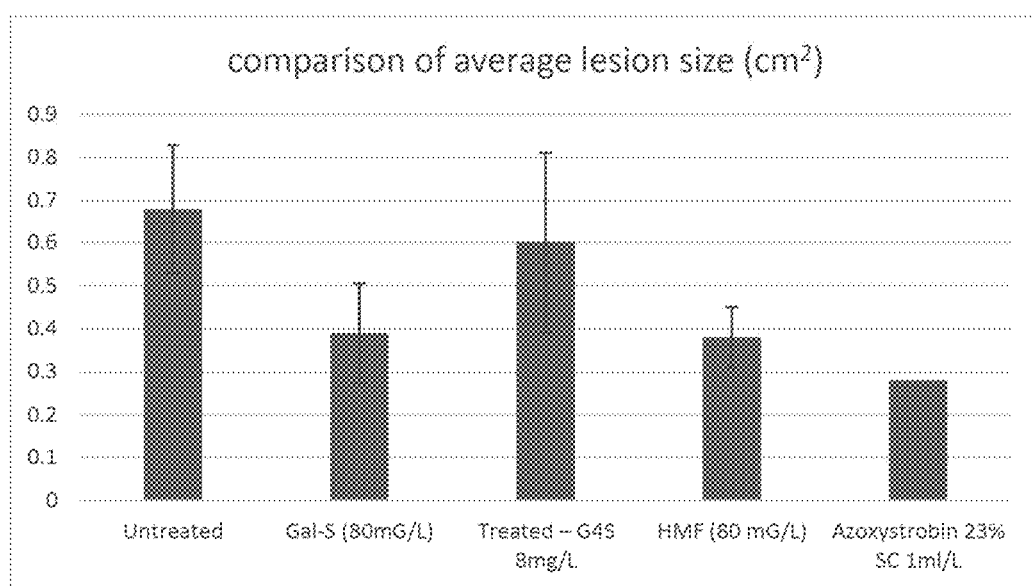
FIG. 8 illustrates the property of Gal-S and HMF by themselves to protect plants from fungal attack in accordance with an embodiment of the present disclosure.

This experiment was conducted as described in the example 13 but the treatments tested were pure, chemically synthesized Gal-S at 80 mg/L, and 8 mg/L, and Hydroxymethylfurfural (HMF) at 80 mg/l along with a commercial fungicide, Azoxystrobin 23% SC at 1 ml/L. It can be noticed from FIG. 8 that both Gal-S and HMF at 80 mg/L concentration show significant reduction in the size of the fungus induced damage compared to the untreated control group. However, Gal-S at 8 mg/L does not show significant reduction in the fungal lesion size. This experiment along with the data presented in Example 13 clearly indicates that, only formulations containing Gal-S above the threshold concentration of 8 mg/L in the final application could confer plant protective activity. This finding is completely novel and is not reported before. Similarly, the property of HMF to protect plants against pathogen attacks is also novel and not reported before. Commercial fungicide Azoxystrobin was included in the experiment as a reference compound.

Figure 9:
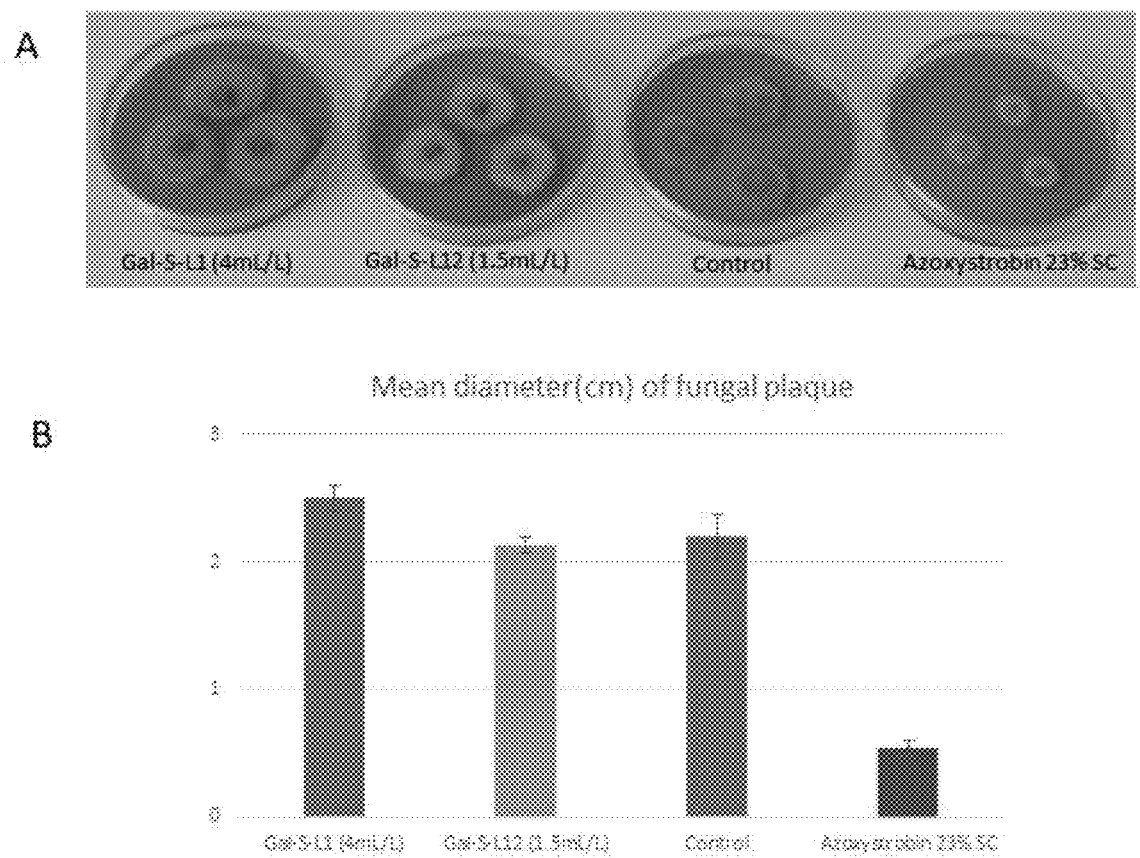
FIG. 9 illustrates that neither the compositions rich in Gal-S nor their constituent components act directly on the plant pathogen and that their plant protective effect is derived by their indirect action on plant innate defence pathways in accordance with an embodiment of the present disclosure.

Example 15: To Show Gal-S-L1 and Gal-S-L12 by Themselves do not Contain any Components that is Directly Active on Fungal Pathogen and that their Plant Protective Effect is Via an Indirect Action on the Plant Itself To answer the questions whether Gal-S-L1 and Gal-S-L12 may themselves have any antifungal compounds leading to their observed plant protective effect the following experiment was devised. In this experiment, sterilized potato-dextrose agar media was incorporated with Gal-S-l1 (at 4 mL/L), Gal-S-L12 (at 1.5 mL/L), and Azoxystrobin 23% SC (at 1.0 mL/L) separately. This medium was spread onto microbiological plates for solidification. The untreated control plates contained only potato-dextrose-agar medium. On day-1, all the above plates were inoculated with equal size of *Alternaria solani* fungal plugs and the plates were further incubated at 24 deg C. for one week. After one week of incubation, the fungal growth was recorded by measuring the diameter of the fungal plaques on each plate (See FIG. 9, (A) and (B)). It can be noted from the data in these figures that the inclusion of Gal-S-L1 liquid formulation or Gal-S-L12 liquid formulation did not have any inhibitory effect on fungal growth while the chemical fungicide, azoxystrobin reduced the fungal plaque size considerably. This example clearly demonstrated that neither the mixtures Gal-S-L1 nor Gal-S-L12 or by inference, their constituent components such as Gal-S. HMF and other oligosaccharides were directly fungicidal in action. The further conclusion that can be drawn from this experiment when taken together with results from the previous two experiments (example 13 and example 14) provides a reason to believe that the plant protective effect of these mixtures is because they induce the native defense systems within the plant which in turn can ward or mitigate the attack by the plant pathogen.

Figure 10:
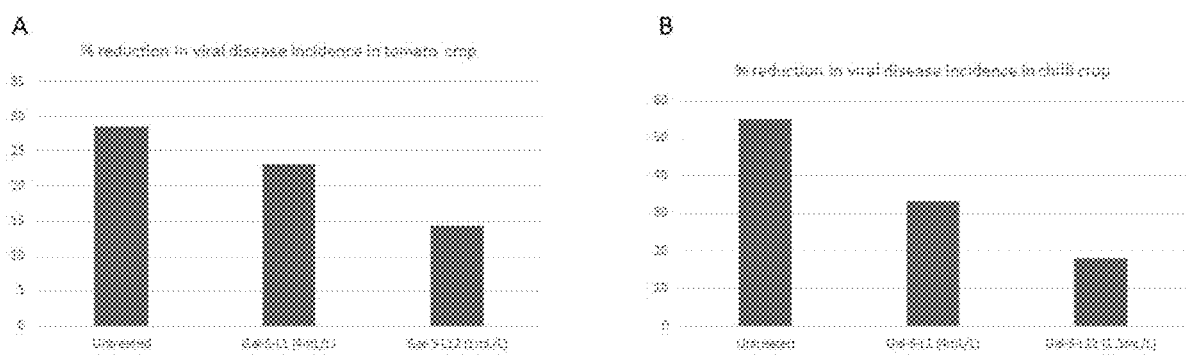
FIG. 10 illustrates how compositions rich in Gal-S can be used to control viral diseases in tomato (A) and chilli plants (B) under field conditions in accordance with an embodiment of the present disclosure.

Example 16: Field Trial Data to Show Reduction in Viral Disease Incidence Upon Prophylactic Spray of Gal-S-L1 and Gal-S-L12 Formulations on Tomato and Chilli Crops In these trials, tomato and chilli plants were cultivated as per the regular agricultural practices in an area prone to natural viral disease incidence. Liquid formulations of Gal-S-L1 and Gal-S-L12 were foliar sprayed in prophylactic manner. Gal-S-L1 (containing Gal-S at 20% of total sugar concentration) was diluted to 4 mL/L of water, while Gal-S-L12 (containing Gal-S at 89% of the total sugar concentration) was diluted to 1.5 mL/L of water before the application on plants. The plants in the control group were sprayed with water only. Three prophylactic sprays were included with an interval of 15 days starting from two weeks after transplanting into the experimental field. The percentage of disease incidence was calculated by recording the total no, of symptomatic plants over total plants in each group. It can be appreciated from the data (FIG. 10) that untreated group shows higher percentage of disease incidence while the plants in either Gal-S-L1 treated group or Gal-S-L12 treated group shows remarkably lower viral disease incidence. Thus, compositions containing Gal-S can be used to control viral diseases in field conditions. It is also interesting to note that among the Gal-S-L1 and Gal-S-L12 treatment groups, the disease incidence was significantly lower in Gal-S-L12 treated group which contains higher percentage of Gal-S (89% of the total sugar concentration).

Figures 11, 12:
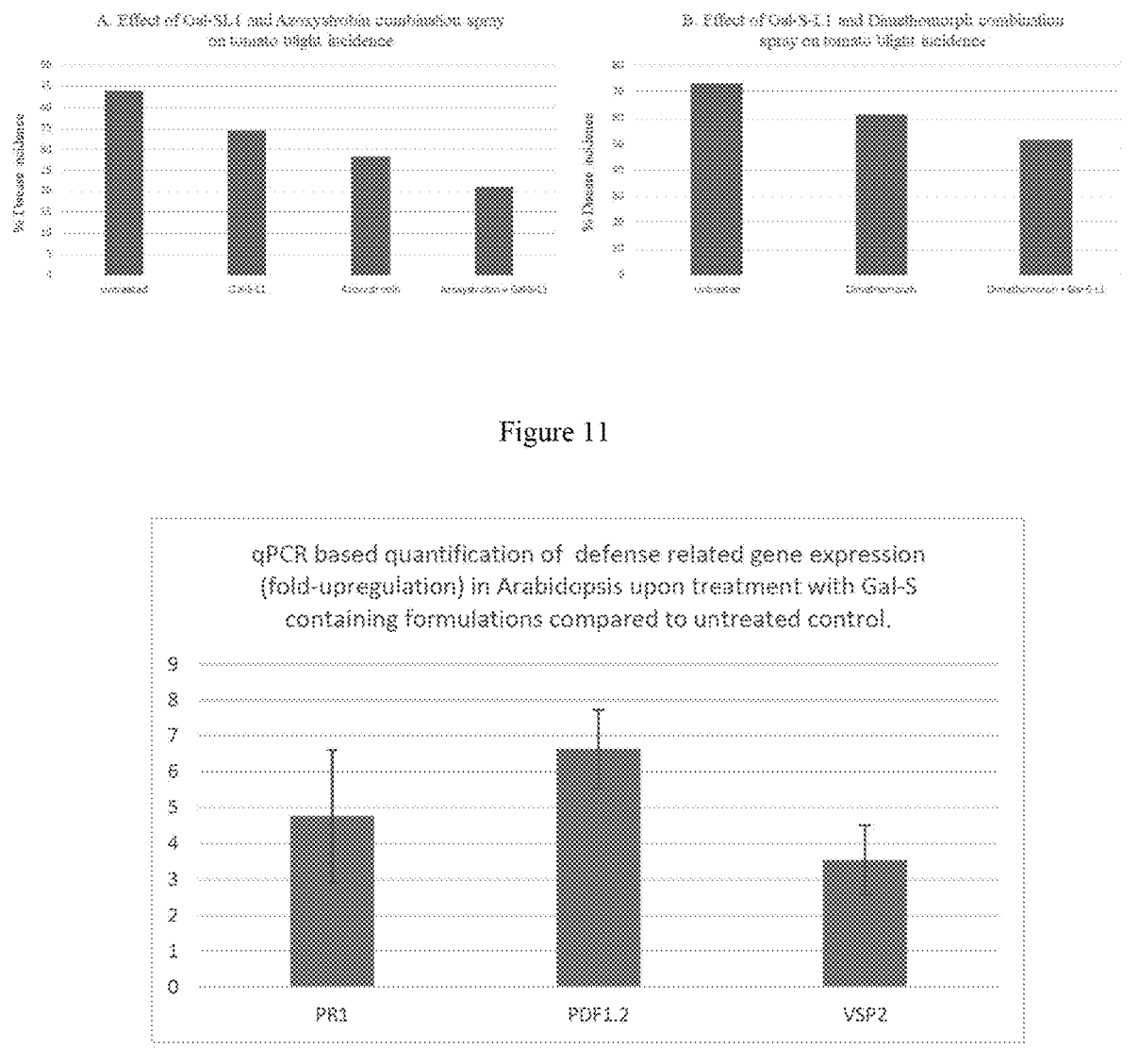

Example 17: Prophylactic Treatment with Gal-S-L1 in Combination with Chemical Fungicides Reduces Tomato Blight Disease Incidence Considerably In this study, the effect of Gal-S-L1 treatment in combination with chemical fungicides azoxystrobin and dimethomorph was explored on tomato crop in the tomato blight vulnerable region. Tomato plants were grown in the field as per the regular agricultural practices. The treatments were imposed on tomato plants after 20 days from transplantation. Three foliar sprays were scheduled with 15 days interval. Gal-S-L1 containing Gal-S at 20% of the total sugar concentration was used at 2 ml/L, while Azoxystrobin 23% SC was used at 1 mL/L. For combination trials, both Gal-S-L1 and azoxystrobin were mixed in sprayer tank at 2 mL/L and 1 mL/L respectively. The percentage of disease incidence was calculated by recording the total no, of symptomatic plants over total plants in each group. It is very apparent from the data (FIG. 11A) that the plants in the group that were treated with tank mix combination of Azoxystrobin and Gal-S-L1 showed the least disease incidence. This may be attributed to combined effect of Azoxystrobin and Gal-S-L1 working via complementary mechanisms to provide plant protective effects. Similarly, tomato plants were treated with dimethomorph 50% WP at a dose of 2 gm/lit, Gal-S-L1 at a dose of 2 ml/L or a combination of dimethomorph 2 gm/lit and Gal-S-L1 at 2 ml/L as a tank mix. Once again, as shown in the data in FIG. 11B, the combination of Dimethomorph and Gal-S-L1 performed better than Dimethomorph alone. In this context. Gal-S-L1 formulation may serve as a suitable additive to use with a variety of chemical fungicides to enhance their efficacy. While the chemical fungicides act directly on the plant pathogen, the Gal-S-L1 activates plant defence systems adding a unique additional mode of action to the plant protection process that is not linked to direct action on the fungal pathogen.

Due to the unique mode of action of Gal-S containing formulations, we expect that these formulations in combination with other plant protective agents like insecticides, microbial extracts, microbes including bacteria, fungi, viruses, bacteriophages would also result in compositions with enhanced plant protection properties.

Example 18: Data Showing Upregulation of Plant Defence Pathways in *Arabidopsis* Plants Upon Treatment with Gal-S Containing Formulations

*Arabidopsis thaliana* is a model plant system that can be used to study mechanisms of actions of various products on plants. In this qPCR-based assay, certain defense marker genes of *Arabidopsis* immune system were quantified in response to Gal-S liquid formulation spray. Primer pairs TCACCCTTATCTTCGCTCTC (SEQ ID NO: 3) and ATGTCCCACTTGGCTTCTCG (SEQ ID NO: 4) were used to monitor PDF1.2 gene while primer pair TGTGAACAGGCAGATGAACC (SEQ ID NO: 5) and GCGATACCGACCTCGTCAA (SEQ ID NO: 6) were used for monitoring VSP2 gene and AATGCTCAAGATAGCCCACAAG (SEQ ID NO: 7) and AATAAGTCACCGCTACCCCAG (SEQ ID NO: 8) primers were used for assaying PR1 gene. In this assay, healthy *A. thaliana* col-0 plants were grown inside a lab growth chamber for 15 days after sowing, one group of these plants were sprayed with liquid formulation containing Gal-S at 20% of the total sugar content, while the control (untreated plants) were sprayed with only water. 48 hrs post-treatment, the leaf samples were collected for RNA and cDNA preparation for qPCR reactions. The data presented in FIG. 12 was normalized against untreated group. PR1, PDF1.2 and VSP2 genes were found to be upregulated considerably. This data provides an insight into the mechanism of action of Gal-S-L1 formulation wherein it may work by upregulation of plant's defense genes. Interestingly. PDF1.2 gene has been annotated as antifungal gene, relating to jasmonic acid pathway while the PR1 gene has been known to be related to systemic acquired resistance pathway in plants. The VSP2 gene has been reported to have anti-insect activity. Thus, this data also corroborates the experimental observations relating to plant protective effects of the formulation (e.g. antiviral and antifungal) efficacy of the Gal-S formulations presented herein.

Figure 13:
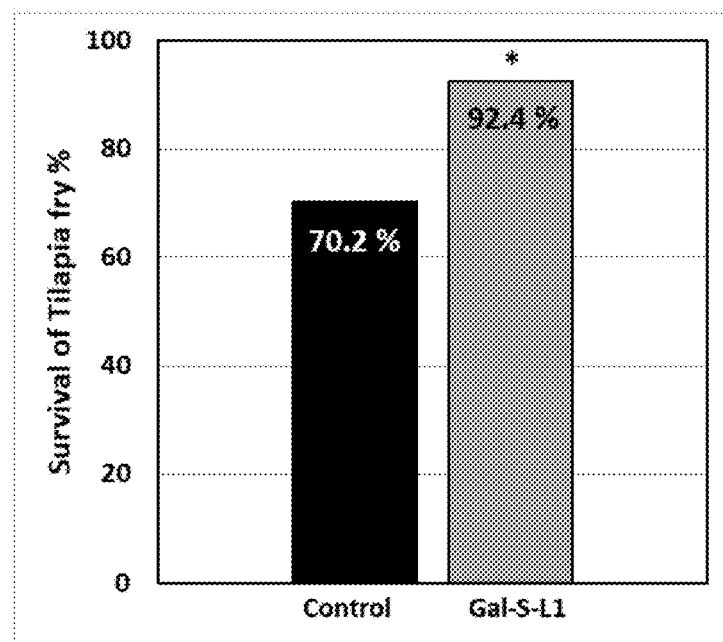
FIG. 13 shows the increase in the survival of Tilapia fry upon treatment with Gal-S-L1 with respect to control (* indicates p-value<0.05. ANOVA) thus showing the ability of Gal-S containing formulation to alleviate abiotic stresses in animals in accordance with an embodiment of the present disclosure.

Example 19—Improved Survival of Tilapia Fry in Outdoor Nursery by Inclusion of Gal-S-L1 in the Feed Tilapia fry (*Oreochromis niloticus* (GIFT—Genetically Modified Farmed Tilapia) of weight 0.1-0.2 gm were stocked at a density of 1 fry/lit into outdoor cement tanks of 150 lit volume in triplicates under shade net conditions. The fish fry were fed with floating feed having 34% protein content at a feeding level of 10% of body weight, thrice a day. No artificial aeration was provided during the experiment. Water exchange was carried out once in 3-4 days. The treated tanks received feed which was premixed with Gal-S-L1 liquid at a dosage of 1 g/kg feed, while the control tanks received the feed without Gal-S-L1. The experiment was conducted for 28 days, and the survival of the fry at the end of this period is shown in FIG. 13. It is observed that the survival of the fish fry increases upon inclusion of Gal-S-L1 in the diet. In the present Example, the premixed feed comprising Gal-S-L1 had an effective dosage of 10 mg/kg feed of Gal-S which was shown to improve survival of the fry.

Example 20—Up-Regulation of Immune-System Genes and Anti-Microbial Peptides in *P. monodon* Shrimp (Post Larvae) after a Single Dose of Gal-S-L1

Post larvae (PL-20) of *P. monodon* were acclimatized in two tanks (control and treatment) for 48 hours. The volume of each tank was 35 lit. Stocking density of PL-20 was 1000 PL per tank. Salinity of each tank was maintained at 15 ppt. Gal-S-L1 was added at a dosage of 0.03 ml/L to the treatment tank, whereas the control tank did not receive any Gal-S-L1.

Figure 15:
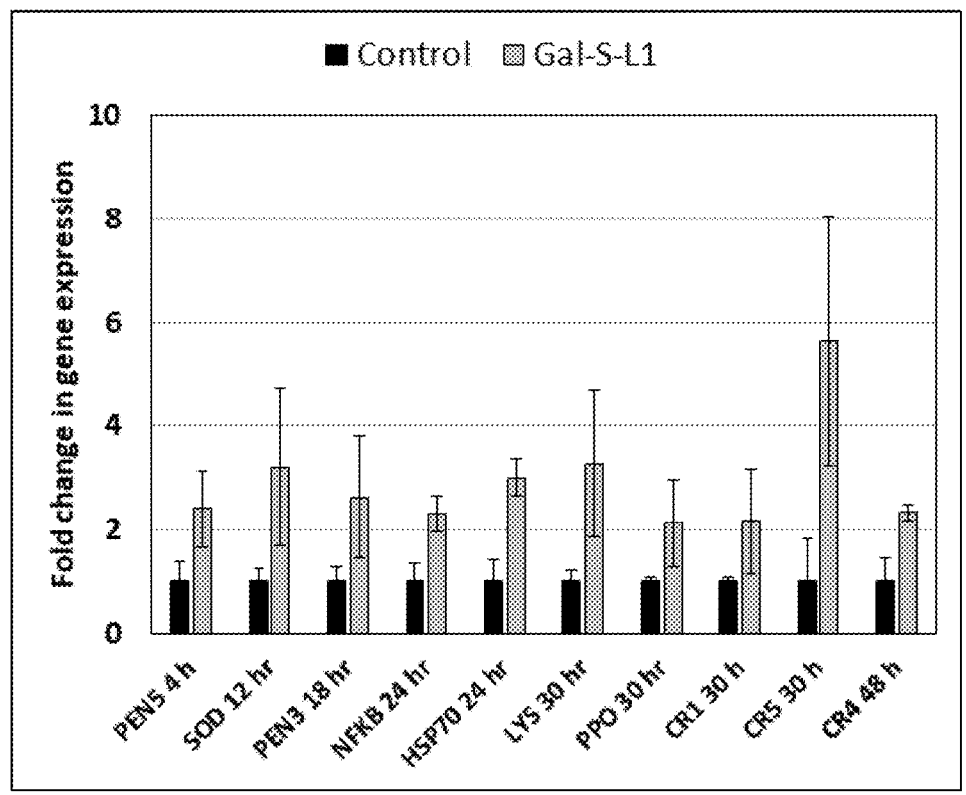
FIG. 15 illustrates the up-regulation of immune-system genes and anti-microbial peptides in *P. monodon* shrimp (post larvae) upon treatment with a Gal-S-L1 containing formulation in accordance with an embodiment of the present disclosure.

Six shrimp (approximately, 60 mg) were collected in 1.5 ml Micro Centrifuge Tubes (MCTs), mixed with 600 µl of TRI reagent and kept on ice. The shrimp tissue was completely homogenized using a tissue macerator. The samples were stored at −80° C. Shrimp samples were collected from both tanks different time intervals after the addition of Gal-S-L1, up to 48 hours. These were subject to RNA extraction and purification by standard protocols, and gene upregulation of Penaeidin 3. Penaeidin 5, Super-oxide dismutase, NF-κB, HSP70, Lysozyme, Prophenoloxidase, Crustin 1, Crustin 4, Crustin 5, EF-1alpha (housekeeping gene) genes were quantified by qPCR using an in-house protocol. The up-regulation of these immune-related and anti-microbial peptide genes in Gal-S-L1 treated shrimp as compared to control is shown in FIG. 15. It can be seen from the graphs that immune related and anti-microbial peptide genes were highly upregulated in the Gal-S-L1 treatment as compared to the control.

Example 21: Improved Humoral Immunity of Commercial Broilers by Inclusion of a Powder Formulation of Gal-S-L1 in the Feed A total of 420 (day old) broiler chickens (Vencobb-400) were randomly divided into 84 pens (in 3 tiered battery brooders) containing 5 birds in each. Sixteen replicate pens were assigned to each treatment in the experiment. All the birds were provided same basal diets phase wise. The results are described here for two treatments i.e. control and treated. In the treatment, a powder formulation having a composition equivalent to Gal-S-L1 was included in the diet of commercial broilers at a dosage of 1 g/kg of poultry feed, while the control had only the basal diet. Birds were wing tagged, weighed and vaccinated with MD vaccine on arrival and offered feed and water ad lib in suitable feeders and waterers. Brooding was done with help of incandescent bulbs up to 21 days. Birds were vaccinated with ND Lasota vaccine on $5^{th}$ and $28^{th}$ day and with IBD vaccine on $10^{th}$ and $16^{th}$ day. The feeding experiment was carried out for 5 weeks.

Figure 16:
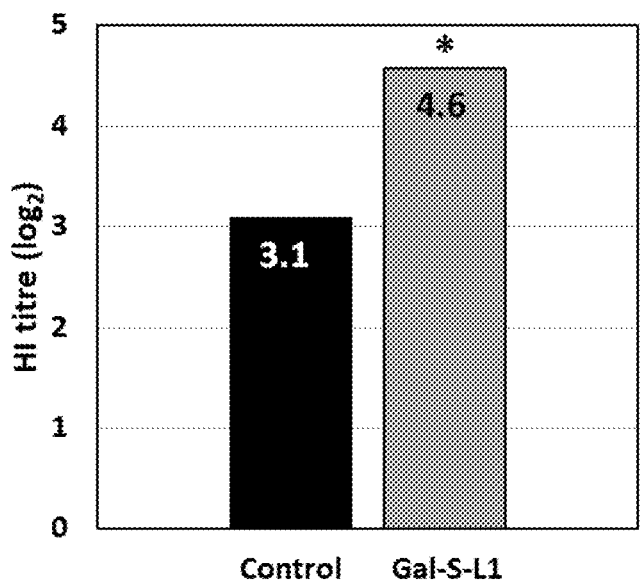
FIG. 16 shows the increase in H1 titre (for serum antibodies against New Castle Disease virus) upon inclusion of a powder formulation of Gal-S-L1 in the broiler feed as compared to control (* indicates p-value<0.05, ANOVA) illustrating the animal protective effect of Gal-S containing formulations in accordance with an embodiment of the present disclosure.

The H1 test was carried out on serum samples collected in $5^{th}$ week of age. The haemagglutination titer of the Newcastle disease virus (NDV) antigen (LaSota virus stock) was adjusted by dilution to contain 4 units of haemagglutination activity. Haemagglutination inhibition titer was determined as the highest dilution of serum samples that inhibited NDV agglutination of chicken RBCs. The increase in HI titre upon inclusion of a powder formulation of Gal-S-L1 in broiler diet as compared to control is shown in FIG. 16 and shows that Gal-S containing formulation shows an animal protective effect when included in the diet.

The table below shows the variation in mortality of birds fed with powder formulation of Gal-S-L1 at a concentration of 1.5 g/kg of feed.

TABLE 2

Mortality of broiler chicken fed with powder formulation of Gal-S-L1

| Powder formulation dose (g/kg of animal feed) | Gal-S (mg/kg of animal feed) | % Mortality |
|---|---|---|
| 0 | 0 | 8.3 |
| 1.5 | 60 | 1.7 |

The formulation improved the mortality when added at 1.5 g/kg of the feed, indicating the animal protective effects of the formulations in the case of broiler chicken.

Example 22: Improved Anti-Oxidant Status of Commercial Broilers by Inclusion of a Powder Formulation of Gal-S-L1 in the Feed The experiment was carried out as mentioned in example 21 above. Glutathione reductase reduces Glutathione disulfide (GSSG) to glutathione (GSH). GSH levels in the serum improve the anti-oxidant status, and facilitate tolerance to oxidative stress. Increased activity of serum Glutathione reductase indicates that the GSH levels in the serum can be restored faster, thereby increasing the tolerance to oxidative stress. Serum Glutathione reductase was estimated according to a standard protocol. FIG. 17 shows the increase in serum Glutathione reductase activity upon inclusion of a powder formulation of Gal-S-L1 w.r.t control. In this assay, one unit of Glutathione reductase enzyme is equivalent to that which can oxidize 1 micro mole of NADPH per min. Thus Gal-S containing formulation can have an animal protective effect by improving the anti-oxidant status of the animal.

Example 23: Upregulation of Defense Pathways in Arabidopsis by Gal-S Formulations is Triggered Only Above a Threshold Concentration of Gal-S Defense gene markers such as PDF 1.2 and VSP2 were quantified in Arabidopsis thaliana plants in response to Gal-S-L1 spray @2 ml/L and Gal-S spray @8 mg/L Gal-S-L1 formulation when applied at 2 ml/L, on the plant would result in Gal-S concentration of 28 mg/L in contact with the plant. The experiment was conducted as per the protocol described in example 18. The data presented in FIG. 18 clearly shows that the relative expression of immune genes PDF1.2 and VSP2 is significantly lower in Gal-S 8 mg/L treatment as compared to Gal-S-L1 formulation. This finding along with the data presented in experiment 14 clearly indicate that the plant protective effects of Gal-S containing formulations would be triggered only above the threshold concentration of 8 mg/L, in the final application.

Advantages of the Present Disclosure:

The present disclosure relates to a composition comprising at least one sulphated galactose. The present disclosure makes an unexpected and surprising finding, which contrary to the published literature, describes compositions rich in the monosaccharide galactose sulphate that confers a property of stimulating the protective systems such as immune response pathways in an organism that provide significant protection against various plant and animal pathogens and abiotic stresses.

Additionally, the present disclosure provides a surprising finding that aforesaid protective and curative activity of stimulating plant and animal immune systems is considerably enhanced by the addition of trace elements such as certain metal ions.

Furthermore, a combination of the galactose sulphate along with metal ions and/or with natural plant defense activators such as salicylic acid and/or amino acids such as beta aminobutyric acid also and sometimes further improve the defense responses tar more that that achieved alone by any of the former substances.

Furthermore, a combination of the galactose sulphate containing compositions along with antifungal agents also enhances the effectiveness of such combinations to provide plant protective effects.

We claim:

1. A composition comprising:
   a) at least one sulphated galactose; and
   b) at least one saccharide selected from a group consisting of: kappa carrabiose, kappa carratriose, kappa carratetraose, iota-carrabiose, iota-carratriose, iota-carratetraose, lambda carrabiose, lambda carratriose, lambda carratetraose, and salts thereof, and
   c) a natural plant defense activator, selected from the group consisting of:
      i) a mixture of salicylic acid and calcium chloride; and
      ii) beta aminobutyric acid,
   wherein the at least one sulphated galactose has a weight percentage in a range of 15-90%, with respect to the total sugar content.

2. The composition as claimed in claim 1, further comprising at least one derivative of a saccharide selected from a group consisting of hydroxy methyl furfural (HMF), levulinic acid, formic acid, and combinations thereof.

3. The composition as claimed in claim 1, wherein the composition has a total sugar content in a range of 25-150 g/l.

4. The composition as claimed in claim 1, wherein the composition has a total sugar content in a range of 100-600 g/kg in a dry form.

5. The composition as claimed in claim 1, wherein the composition further comprises at least one substance selected from a group consisting of solvent, diluent, emulsifiers, stabilizers, animal feed, and combinations thereof.

6. The composition as claimed in claim 1, wherein the at least one sulphated galactose is having a weight percentage in a range of 5-90% of total solid content of the composition.

7. The composition as claimed in claim 1, wherein the at least one sulphated galactose to the at least one saccharide has a weight ratio in a range of 1:5 to 50:1.

8. The composition as claimed in claim 2, wherein the at least one sulphated galactose to the at least one derivative of a saccharide has a weight ratio in a range of 9:1 to 2:1.

9. The composition as claimed in claim 1, wherein the composition further comprises a trace element.

10. The composition as claimed in claim 9, wherein the trace element is selected from a group consisting of boron, zinc, iron, manganese, magnesium, molybdenum, calcium, potassium, selenium, copper combinations thereof and their salts.

11. The composition as claimed in claim 1, wherein the composition is obtained by processing carrageenan or processed Eucheuma or semi-refined carrageenan.

12. The composition as claimed in claim 1, wherein the composition is obtained by processing carrageenan containing red seaweed.

13. The composition as claimed in claim 1, wherein the composition provides protection to plants against biotic stress.

14. The composition as claimed in claim 1, wherein the composition provides protection to animals against biotic and abiotic stress.

15. The composition as claimed in claim 1 for use as plant defense pathway activator.

16. The composition as claimed in claim 1 for use in protecting plants from infections and biotic stress.

17. The composition of claim 15, wherein the composition comprises at least one sulphated galactose having a concentration of at least 10 mg/L with respect to the composition which is contacted with the plant or parts of the plant.

18. A process for preparing the composition as claimed in claim 1, said process comprising:
   (a) contacting a substance having a mixture of polysaccharides with water to obtain a slurry;
   b) depolymerizing the slurry by hydrolysis to obtain a hydrolysate;
   c) concentrating the hydrolysate to achieve a sugar concentration having Brix value in a range of 18-35 to obtain the composition in a liquid form, or optionally drying the hydrolysate to obtain the composition in a powder form.

19. The process as claimed in claim 18, said process comprising:
   (a) contacting red seaweed with water to obtain to obtain a slurry with a total solid content in the range of 5-20%;
   (b) depolymerizing the slurry in a pH in a range of 1.0-4.0 at a temperature in a range of 50-180° C., and pressure in a range of 0.5-10 atmospheric pressure for a time in a range of 10 minutes-5 hours to obtain a hydrolysate;
   (c) concentrating the hydrolysate to achieve a sugar concentration having Brix value in a range of 18-35 to obtain the composition in a liquid form;
   (d) optionally drying the hydrolysate to obtain the composition in a powder form.

20. The process as claimed in claim 18, said process comprising:
(a) contacting carrageenan with water to obtain to obtain a slurry with a total solid content in the range of 5-20%;
(b) depolymerizing the slurry in a pH in a range of 1.0-4.0 at a temperature in a range of 50-180° C., and pressure in a range of 0.5-10 atmospheric pressure for a time in a range of 10 minutes-5 hours to obtain a hydrolysate;
(c) concentrating the hydrolysate to achieve a sugar concentration having Brix value in a range of 18-35 to obtain the composition;
d) optionally drying the hydrolysate to obtain the composition in a powder form.

21. A method for treating a plant, said method comprising: (a) obtaining the composition of claim 1; and (b) contacting the composition with a plant or parts of a plant, for treating the plant.

22. The method as claimed in claim 21, wherein the composition comprises at least one sulphated galactose having a concentration of at least 10 mg/L with respect to the composition.

23. The method as claimed in claim 21, wherein the composition is contacted with the plant by a method selected from a group consisting of foliar application, soil application, seed treatment, injection onto plant tissues, and combinations thereof.

24. The method as claimed in claim 21, wherein the method comprises contacting the composition with the plant by foliar application, said foliar application comprises contacting the composition at a rate of 50-1000 ml/acre of crop.

25. The method as claimed in claim 21, wherein the foliar application is carried out in vegetative state of plant, and the application is done at 10-15 days after transplantation, subsequent application is done at an interval of 10-15 days till the onset of flowering and fruiting.

26. The method as claimed in claim 21, wherein contacting is in combination with at least one penetrating agent selected from a group consisting of anionic surfactant, ionic, non-ionic surfactant, polysorbates, sodium dodecyl sulphate, lauryl dimethyl amine oxide, cetyltrimethylammonium bromide, polyethoxyated alcohols, polyoxyethylene sorbitan, octoxynol, N,N-dimethyldodecylamine-N-oxide, hexadecyltrimethylammonium bromide, polyoxyl 10 lauryl ether, Brij 721, bile salts, polyoxyl castor oil, nonylphenol ethoxylate, cyclodextrins, lecithin, methyl benzethonium chloride, and combinations thereof.

27. The method as claimed in claim 21, wherein contacting is in combination with at least one bio-enhancer selected from a group consisting of seaweed extract, protein hydrolysates, humic acid, fulvic acid, microbial extracts, and bio-fertilizer.

28. The method as claimed in claim 21, wherein contacting is in combination with at least one plant protective agent selected from a group consisting of consisting of fungicides, insecticides, microbial extracts, microbes including bacteria, fungi, viruses, bacteriophages etc.

29. A method for treating an animal, said method comprising:
(a) obtaining the composition of claim 1; and
b) administering the composition to an animal or parts of an animal, for treating the animal.

30. The method as claimed in claim 29, where in the method comprises addition of composition: a) to the water used by the animal or b) by feed infusion or c) topical application or d) injecting the composition into animal tissues and or combinations thereof.

31. The method as claimed in claim 29, wherein the composition comprises at least one sulphated galactose having a concentration of at least 10 mg/kg with respect to the feed being given to the animal.

32. The method as claimed in claim 29, wherein the composition comprises at least one sulphated galactose having a concentration of at least 30 mg/tonne with respect to the culture water in which the animal is grown.

* * * * *

SEQUENCE LISTING

<160> NUMBER OF SEQ ID NOS: 8

<210> SEQ ID NO 1
<211> LENGTH: 20

```
<212> TYPE: DNA
<213> ORGANISM: Artificial Sequence
<220> FEATURE:
<223> OTHER INFORMATION: SEQ ID NO: 1 depicts forward primer sequence
      to amplify PRSV NiB gene

<400> SEQUENCE: 1
agtcggcccg aagcaattt                                               20

<210> SEQ ID NO 2
<211> LENGTH: 27
<212> TYPE: DNA
<213> ORGANISM: Artificial Sequence
<220> FEATURE:
<223> OTHER INFORMATION: SEQ ID NO: 2 depicts reverse primer sequence
      to amplify PRSV NiB gene

<400> SEQUENCE: 2
ctcatcacac tcaagatagt tcctgaa                                      27

<210> SEQ ID NO 3
<211> LENGTH: 21
<212> TYPE: DNA
<213> ORGANISM: Artificial Sequence
<220> FEATURE:
<223> OTHER INFORMATION: SEQ ID NO: 3 depicts forward primer sequence
      to amplify PDF 1.2 gene

<400> SEQUENCE: 3
tcacccttat cttcgctgct c                                            21

<210> SEQ ID NO 4
<211> LENGTH: 20
<212> TYPE: DNA
<213> ORGANISM: Artificial Sequence
<220> FEATURE:
<223> OTHER INFORMATION: SEQ ID NO: 4 depicts reverse primer sequence
      to amplify PDF 1.2 gene

<400> SEQUENCE: 4
atgtcccact tggcttctcg                                              20

<210> SEQ ID NO 5
<211> LENGTH: 20
<212> TYPE: DNA
<213> ORGANISM: Artificial Sequence
<220> FEATURE:
<223> OTHER INFORMATION: SEQ ID NO: 5 depicts forward primer sequence
      to amplify VSP gene

<400> SEQUENCE: 5
tgtgaacagg cagatgaacc                                              20

<210> SEQ ID NO 6
<211> LENGTH: 19
<212> TYPE: DNA
<213> ORGANISM: Artificial Sequence
<220> FEATURE:
<223> OTHER INFORMATION: SEQ ID NO: 6 depicts reverse primer sequence
      to amplify VSP gene

<400> SEQUENCE: 6
gcgataccga tctcgtcaa                                               19

<210> SEQ ID NO 7
<211> LENGTH: 22
<212> TYPE: DNA
```

```
<213> ORGANISM: Artificial Sequence
<220> FEATURE:
<223> OTHER INFORMATION: SEQ ID NO: 7 depicts forward primer sequence
      to amplify PR 1 gene

<400> SEQUENCE: 7
aatgctcaag atagcccaca ag                                            22

<210> SEQ ID NO 8
<211> LENGTH: 21
<212> TYPE: DNA
<213> ORGANISM: Artificial Sequence
<220> FEATURE:
<223> OTHER INFORMATION: SEQ ID NO: 8 depicts reverse primer sequence
      to amplify PR 1 gene

<400> SEQUENCE: 8
aataagtcac cgctacccca g                                             21
```